United States Patent [19]
Sugiura et al.

[11] Patent Number: 5,847,822
[45] Date of Patent: Dec. 8, 1998

[54] OPTICAL ELEMENT INSPECTING APPARATUS

[75] Inventors: Masayuki Sugiura; Masato Hara; Toshihiro Nakayama; Atsushi Kida, all of Tokyo, Japan

[73] Assignee: Asahi Kogaku Kogyo Kabushiki Kaisha, Tokyo, Japan

[21] Appl. No.: 702,042

[22] Filed: Aug. 23, 1996

[30] Foreign Application Priority Data

Aug. 29, 1995 [JP] Japan .................................. 7-220831
Aug. 29, 1995 [JP] Japan .................................. 7-220832
Sep. 6, 1995 [JP] Japan .................................. 7-229242

[51] Int. Cl.$^6$ ............................. G01N 21/00; G01B 9/00
[52] U.S. Cl. ........................................... 356/239; 356/124
[58] Field of Search ................................... 356/124–127, 356/237, 239

[56] References Cited

U.S. PATENT DOCUMENTS 5,216,481  6/1993  Minato .................................. 356/240

*Primary Examiner*—Frank G. Font
*Assistant Examiner*—Amanda Merlino
*Attorney, Agent, or Firm*—Greenblum & Bernstein P.L.C.

[57] ABSTRACT

An optical element inspecting apparatus for detecting an optical defect of an optical element to be inspected. The inspection apparatus includes a diffusion plate, a device for emitting light towards the diffusion plate such that a diffused light diffused by the diffusion plate is incident upon an optical system including at least the optical element, and a device for intercepting a part of the diffused light so that the part of the diffused light is not incident upon the optical system. The light intercepting device is positioned substantially in a plane perpendicular to an optical axis of the optical system, between the optical system and the diffusion plate, substantially at a focal point of the optical system.

38 Claims, 17 Drawing Sheets

OPTICAL ELEMENT INSPECTING APPARATUS

BACKGROUND OF THE INVENTION

1. Field of the Invention

The present invention relates to an optical element inspecting apparatus for detecting an optical defect, such as an abnormality in a refractive index of a lens or the like.

2. Description of the Related Art

An optical element such as a lens or a prism, etc., is generally designed such that light incident thereupon is refracted to produce parallel beams of light, or is converged onto a point or line, or is diverged. However, if the optical element has an irregular refracting power distribution, due to a defective formation thereof, or if the optical element is scratched during handling thereof by an operator, or if a foreign matter is attached to the surface of the optical element, the light incident upon the optical element become disturbed, thus resulting in a failure to obtain a desired optical property. In particular, a lens or prism which is made of a resin mold using a molding die tends to have, on its surface, depressions caused by a separation of the resin material from the surface of the molding die, or flaw marks in the form of ripples, caused by a contraction of the resin. In addition, the lens or prism tends to have therein a locally irregular resin density portion, caused by jetting, i.e., a turbulent flow of molten resin during the molding of plastics which results in some portions of the lens having a different density compared with other portions of the lens. Thus, it is necessary to effectively detect these defects.

To this end, sensory tests relying upon an operator's eyesight have been carried out using a strain gage or a light source for a slide projector.

The strain gage consists of crossed polarization gratings in which a member to be inspected, e.g., an optical element, is positioned. The transmittance of light passed through the crossed polarization gratings and the optical element varies depending upon the refractive index of the optical element. Consequently, an abnormality of the refractive index of the optical element can be visually detected since the portion of the optical element having the abnormality is perceived having a different depth of color as compared with other portions of the optical element.

In an inspection using the light source for the slide projector, the optical element is illuminated with light emitted from the light source, so that the surface of the optical element can be observed by an operator outside of the optical path, to find a scratch or flaw formed on the surface of the optical element, or a foreign matter attached to the surface of the optical element.

However, in the sensory inspection using an operator's eyesight, there is no definite objective criterion to discriminate a defective product from a non-defective product. Consequently, in the case that the inspection is executed by more than one inspector, the judgement (inspection result) may vary depending upon the inspector. Namely, the same product may be judged "defective" by one inspector and "non-defective" by another inspector. Consequently, a non-defective product may unnecessarily be wasted or destroyed. Also, if a defective product is included in a batch of non-defective products, the overall quality of the whole batch is deteriorated. Moreover, if the same inspector checks the products, the criterion tends to become strict through practice, so that the probability that a non-defective product is mistakenly judged to be a defective product increases.

Particularly, in the inspection using the strain gage, an operator cannot perceive the shape of a defect on an optical element from seeing the depth of color of the defect, i.e., a defect is not seen as brighter or darker compared with other portions of the optical element. Hence, in the inspection using the strain gage, it is impossible to determine the type of defect, the degree of defect or the like, even if the optical element can be identified as a defective optical element.

In addition, the strain gage can only detect the abnormality of a refractive index of an optical element, but cannot detect a scratch or flaw formed on the surface of the optical element, or a foreign matter attached to the surface of the optical element. Therefore, in order to further detect such a scratch or a foreign matter after detecting that an abnormality of the refractive index exists using the strain gage, the optical member needs to be removed from the strain gage to be inspected using the light source for the slide projector or like. Further, as noted above, the source is separately provided from the strain gage. In other words, in the sensory inspection using the strain gage, the abnormality of a refractive index of an optical element, a scratch or flaw formed on the surface of the optical element, and/or a foreign matter affixed to the surface of the optical element cannot be detected in a single inspection operation.

SUMMARY OF THE INVENTION

An object of the present invention is to provide an optical element inspecting apparatus in which the quality of an optical element can be judged in accordance with an objective criterion.

Another object of the present invention is to provide an optical element inspecting apparatus which makes it possible to indicate not only an abnormality of a refractive index of an optical element, but also a defect formed on the surface of the optical element, in a single inspection operation, and which emphasizes defects to make it possible to realize a precise judgement as to whether the optical element is defective or non-defective, and which makes it possible to further indicate the type and degree of the defect.

Yet another object of the present invention is to provide an optical element inspecting apparatus which makes it possible to indicate not only an abnormality of the refractive index of an optical element, but also indicate the defect formed on the surface of the optical element, in a single inspection operation, and which emphasizes defects in various directions to thereby make it possible to realize a precise judgement as to whether the optical element is defective or non-defective, and which also makes it possible to further indicate the type and degree of the defect.

To achieve the objects mentioned above, according to an aspect of the present invention, there is provided an optical element inspecting apparatus for detecting an optical defect of an optical element to be inspected. The optical element inspecting apparatus includes a diffusion plate, a device for emitting light towards the diffusion plate such that a diffused light diffused by the diffusion plate is incident upon an optical system including at least the optical element, and a device for intercepting a part of the diffused light so that the part of the diffused light is not incident upon the optical system. The light intercepting device is positioned substantially in a plane perpendicular to an optical axis of the optical system, between the optical system and the diffusion plate, substantially at a focal point of the optical system.

The optical system may consist of only the optical element, or can be in the form of a converging lens system, or alternatively may be a converging lens system consisting of the optical element, in the form of a concave lens, and a correction lens, in the form of a convex lens.

The light intercepting device preferably contacts the diffusion plate. The light intercepting device may be in the form of an opaque plate. Alternatively, the light intercepting device may be in the form of a transparent member and an opaque member formed on the transparent member. The opaque member is preferably an opaque paint which is painted on the transparent member.

Preferably, an image pickup device is provided to pick up an image of light transmitted through the optical system. The image pickup device includes an image pickup lens which converges the light transmitted through the optical system. The image pickup device is preferably positioned at a position which is optically equivalent to a position where a surface of the optical element is located.

The diffusion plate may be guided along the optical axis, so that a position of the light intercepting device can be adjusted along the optical axis.

A device for rotating the light intercepting device may be provided in the plane perpendicular to the optical axis.

Preferably, an image pickup device, a digitizing device and a judging device are also provided. The image pickup device picks up an image of light transmitted through the optical system. The digitizing device represents a portion of the image which corresponds to the optical defect of the optical element by a numerical value. The judging device judges whether the numerical value is above a predetermined reference value.

According to another aspect of the present invention, an optical element inspecting apparatus for detecting an optical defect of an optical element to be inspected is provided. The optical element inspecting apparatus includes an illuminating device. A diffusion plate is illuminated with light emitted from the illuminating device. A plate is provided having an opaque portion that is fixed on the diffusion plate. An image pickup device picks up an image of the optical element. A display is also provided on which the image picked up by the image pickup device means is indicated. The plate having the opaque portion is positioned substantially at a focal point of a converging optical system which includes at least the optical element.

In yet another aspect of the present invention, an optical lens inspecting apparatus for detecting a defect of an optical element to be inspected is provided. The optical lens inspecting apparatus includes a light source, a device for diffusing light emitted from the light source, and a device for intercepting a part of the light emitted from the diffusing device. The intercepting device is positioned substantially at a focal point of a converging optical system which includes at least the optical element.

In a further aspect of the present invention, an optical element inspecting apparatus for detecting an optical defect of an optical element to be inspected is provided. The optical element inspecting apparatus includes a surface illuminant for emitting light towards a converging optical system which includes at least the optical element, and a device for intercepting a part of the light so that the part of the light does not reach the converging optical system. The light intercepting device is positioned substantially in a plane perpendicular to an optical axis of the converging optical system, between the converging optical system and the surface illuminant, substantially at a focal point of the converging optical system.

The present disclosure relates to subject matter contained in Japanese Patent Applications No.7-220831 (filed on Aug. 29, 1995), No.7-220832 (filed on Aug. 29, 1995) and No.7-229242 (filed on Sep. 6, 1995) which are expressly incorporated herein by reference in their entireties.

BRIEF DESCRIPTION OF THE DRAWINGS

The file of this patent contains at least one drawing executed in color.

The invention will be described below in detail with reference to the accompanying drawings, in which similar elements are indicated by similar reference numerals, and wherein.

DESCRIPTION OF THE PREFERRED EMBODIMENTS

Figure 1:
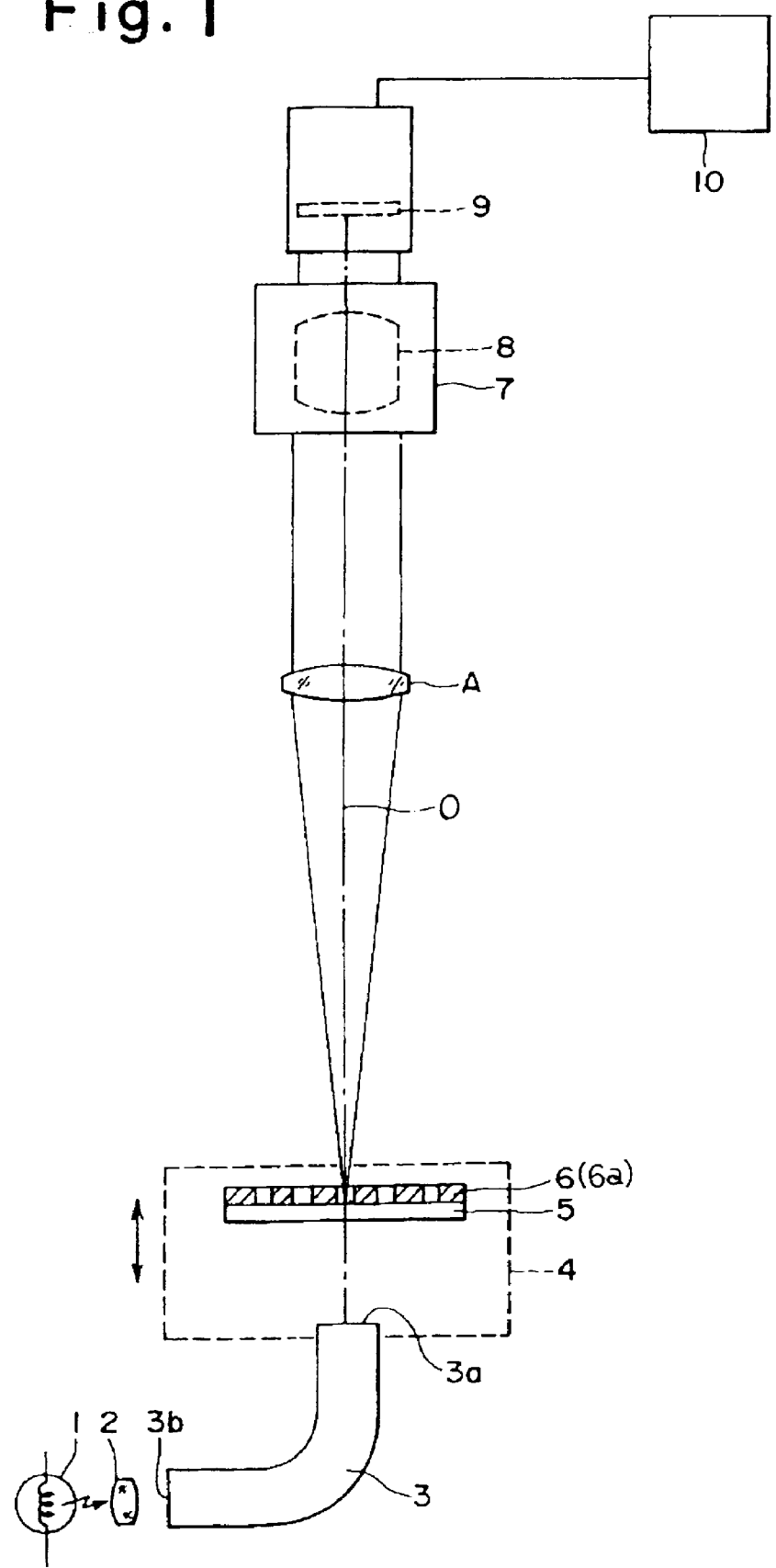
FIG. 1 is a schematic view of a first embodiment of an optical element inspecting apparatus to which the present invention is applied.
Figure 2:
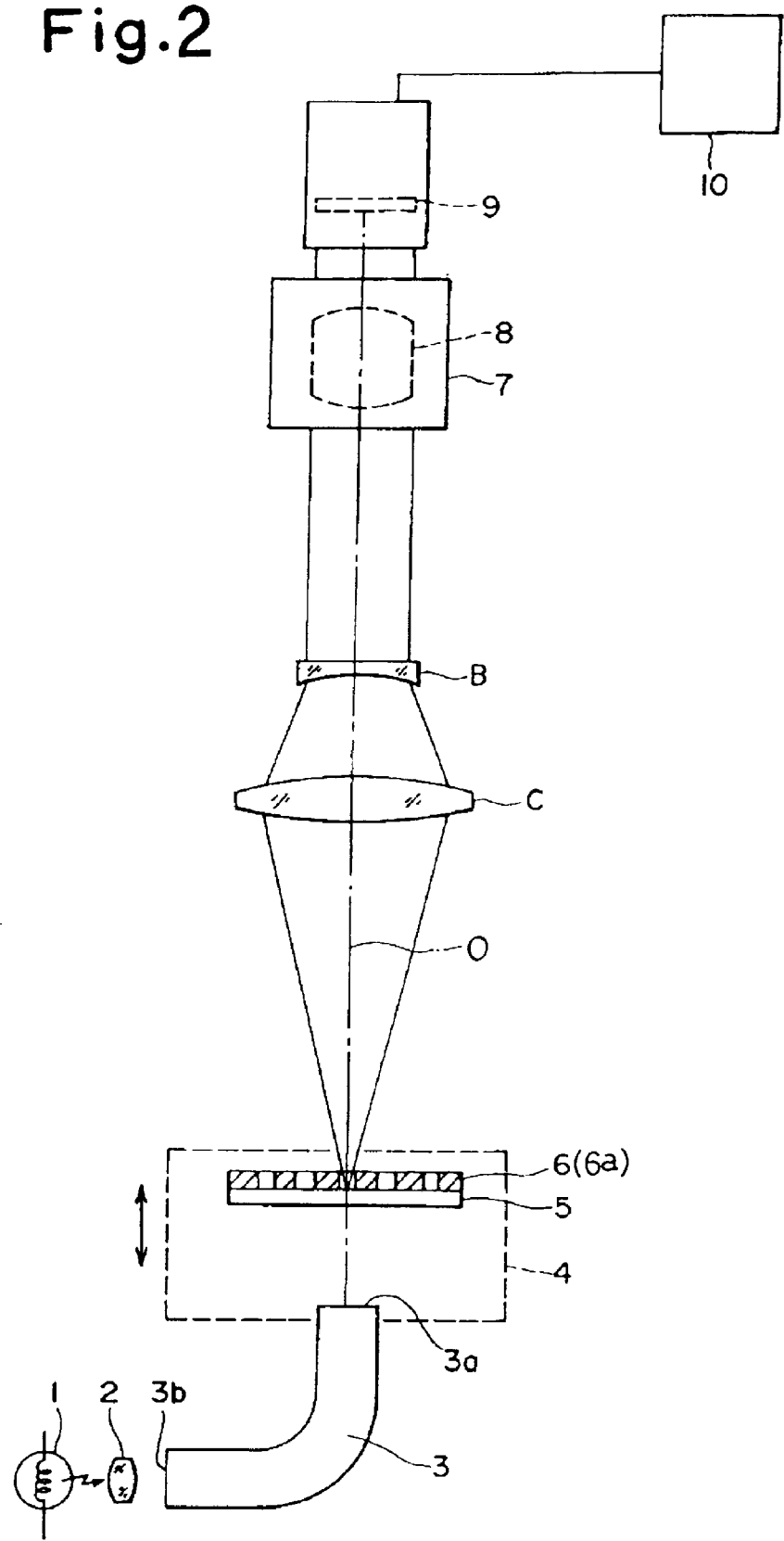
FIG. 2 is a schematic view of the optical element inspecting apparatus shown in FIG. 1, applied to a concave lens.

Optical Arrangement of an Optical Element Inspecting Apparatus of First Embodiment FIGS. 1 and 2 show a first embodiment of an optical element inspecting apparatus for detecting an optical defect of the optical element, to which the present invention is applied. The optical defect may be an abnormality in a refractive index or refracting power (irregular refractive index or refracting power) of the optical element, or a surface defect such as a scratch formed on the surface of the optical element, a dust affixed to the surface of the optical element, etc.

In FIGS. 1 and 2, an illumination unit 4 and a photographing device 7, which constitute an optical element inspecting apparatus, are aligned along an optical axis O.

The photographing device 7 serves as an image pickup means (apparatus). The photographing device 7 consists of a photographing lens 8, which constitutes a positive lens system as a whole, and an image pickup element 9. The image pickup element 9 consists of a CCD area sensor which picks up an image formed by light converged by the photographing lens 8. The image pickup element 9 may consist of an image pickup tube. The image picked up by the image pickup element 9 is input to a CRT display 10 to visually indicate the image thereon.

The illumination unit 4 is guided, by a guiding device (not shown), along the optical axis O. The illumination unit 4 is provided therein with a circular diffusion disc 5. The circular diffusion disc 5 functions as a diffusion screen and is made of a translucent member. The circular diffusion disc 5 is fixed on the illumination unit 4 coaxial to the optical axis O.

The diffusion disc 5 is provided, on the surface facing in the direction of the image pickup apparatus 7, with a light intercepting plate 6 integrally cemented thereto. The light intercepting plate 6 serves as a light intercepting means.

Figure 3:
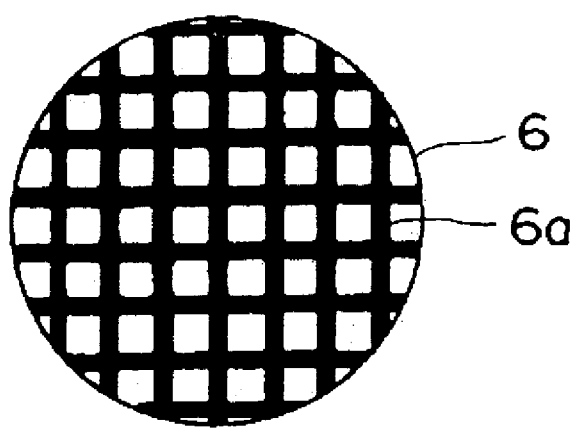
FIG. 3 is a front elevational view of a light intercepting pattern shown in FIG. 1 or 2.

The light intercepting plate 6 is constructed from a very thin transparent optical glass or plastic and is provided with a light interceptive pattern 6a, shown in FIG. 3, that is printed on the light intercepting plate 6 using black paint. As shown in FIG. 3, the light interceptive pattern 6a is formed in the shape of a grille or grating. Light diffused by the diffusion disc 5 is partially intercepted by the light intercepting plate 6 at the portions thereof on which the light interceptive pattern 6a is printed. The remaining portion of the diffused light passes through the light intercepting plate 6 at the portions thereof on which the light interceptive pattern 6a is not printed, namely, without being intercepted by the light intercepting plate 6.

An optical fiber bundle 3 is connected at a front end 3a thereof to the illumination unit 4 at the rear of the diffusion disc 5. A base end 3b of the optical fiber bundle 3 is opposed to a light source apparatus consisting of a white light lamp 1 and a condenser lens 2. White light emitted from the white light lamp 1 is condensed by the condenser lens 2 and is made incident upon the base end 3b of the optical fiber bundle 3. The white light is transmitted through the optical fiber bundle 3 before being emitted from the front end 3a toward the diffusion disc 5. Namely, the light interceptive pattern 6a of the light intercepting plate 6 is illuminated from behind.

The length of the optical fiber bundle 3 is sufficiently longer than the amount of displacement of the illumination unit 4. Thus, the optical fiber bundle 3 is extended in accordance with the movement of the illumination unit 4 so as to continuously illuminate the light interceptive pattern 6a of the light intercepting plate 6.

The optical element to be inspected is positioned coaxial to the optical axis O between the image pickup apparatus 7 and the illumination unit 4. Namely, if the optical element to be inspected is a convex lens "A", the optical element is positioned such that the focal point thereof is coincident with the position of the light interceptive pattern 6a of the light intercepting plate 6, as shown in FIG. 1. If the optical element to be inspected is a concave lens "B", a correcting lens "C" made of a convex lens having a power (absolute value) greater than the power (absolute value) of the concave lens "B" is positioned between the concave lens "B" and the illumination unit 4, as shown in FIG. 2. The concave lens "B" and the correction lens "C" define a converging lens system (converging optical system) whose resultant focal point is coincident with the position of the light interceptive pattern 6a of the light intercepting plate 6. Namely, the focal point of the optical system including the optical element to be inspected is identical to the position of the light intercepting means. The optical element to be inspected may be any kind of optical element, such as a convex lens, a concave lens, a prism, a concave mirror, a convex mirror, a plane-parallel plate, etc. The optical element may be made of glass or plastic.

If the optical element to be inspected is a flat plate (not shown), the correction lens "C" is provided so that the focal point of the correction lens "C" is coincident with the position of the light interceptive pattern 6a. The flat plate to be inspected is positioned between the correction lens "C" and the image pickup apparatus 7. Moreover, if the optical element to be inspected is a reflection prism (not shown), such as a Porro prism or a roof prism, etc., the correction lens "C" is provided so that the focal point of the correction lens "C" is coincident with the position of the light interceptive pattern 6a. The reflection prism to be inspected is positioned between the correction lens "C" and the image pickup apparatus 7 which is located on the optical axis of that light emitted from the reflection prism. If the optical element to be inspected is a reflection mirror (not shown), the positional relationship between the optical illuminating system 4 and the reflection mirror (and the correction lens "C") is the same as the foregoing, and a beam splitter or a half-mirror (not shown) is provided between the illumination unit 4 and the reflection mirror, in the path of light beams reflected by the reflecting mirror. The image pickup apparatus 7 is provided in the optical path of the reflected light split by the beam splitter or the half-mirror.

If the optical element to be inspected (i.e., the convex lens "A" or the concave lens "B" and the correction lens "C") is positioned as mentioned above, the light emitted from the optical element (i.e., the convex lens "A" or the concave lens "B") becomes parallel beams of light so long as the optical element is a non-defective product. Consequently, if the light interceptive pattern 6a of the light intercepting plate 6 is viewed from the side of the image pickup apparatus 7, the light interceptive pattern 6a appears to be at infinity.

If the focal point of the optical element "A" (or the resultant focal point of the lens group consisting of the optical element "B" and the correction lens "C") is shifted toward the image pickup apparatus 7 from the position of the light interceptive pattern 6a, an inverted image (real image) of the light interceptive pattern 6a is formed in an area defined between the optical element "A" (or "B") and the image pickup lens 8 of the image pickup apparatus 7. The inverted image of the light interceptive pattern 6a is relayed through the image pickup lens 8 to form an erect image (real image) of the light interceptive pattern 6a in the area defined on the side of the image pickup lens 8 adjacent to the image pickup element 9. Conversely, if the focal point of the optical element "A" (or the resultant focal point of the lens group consisting of the optical element "B" and the correction lens "C") is shifted toward the optical fiber bundle 3 from the position of the light interceptive pattern 6a, an erect image (virtual image) of the light interceptive pattern 6a is formed in an area defined on the side of the light intercepting plate 6 adjacent to the optical fiber bundle 3. The erect image (virtual image) of the light interceptive pattern 6a is relayed through the image pickup lens 8 to form an inverted image (real image) of the light interceptive pattern 6a in the area defined on the side of the image pickup lens 8 adjacent to the image pickup element 9. Namely, the focal point of the optical element "A" to be examined (or the resultant focal point of the lens group consisting of the optical element "B" to be examined and the correction lens "C") defines a boundary position in which the object image (image of the light interceptive pattern 6a) is formed as an erect image or an inverted image in the area defined on the side of the image pickup lens 8 adjacent to the image pickup element 9. Namely, in this position, the image is optically unstable.

The distance between the optical element to be inspected and the image pickup lens 8 is set to be as long as possible, so that the inverted image (real image) of the light interceptive pattern 6a can be formed between the optical element and the image pickup lens 8 (precisely speaking, between the focal points thereof), even if the focal point of the optical element "A" (or the resultant focal point of the lens group consisting of the optical element "B" and the correction lens "C") is slightly shifted toward the image pickup apparatus 7 from the position of the light interceptive pattern 6a. The image pickup element 9 is located at an intermediate position of the erect image forming position (average position) and the inverted image forming position (average position), so that the erect or inverted image formed by the image pickup lens 8 can be picked up clearly to some extent. The intermediate position is optically equivalent to the surface of the optical element "A" or "B" with respect to the image pickup lens 8.

Thus, a real image (inverted image) α of the peripheral edge of the optical element to be examined is always formed on the image pickup element 9, and a slightly blurred real image (inverted image) β of the light interceptive pattern 6a, which is directly visible without passing through the optical element, is formed around the real image α, as can be seen in FIGS. 4A through 4E.

Figure 4A:
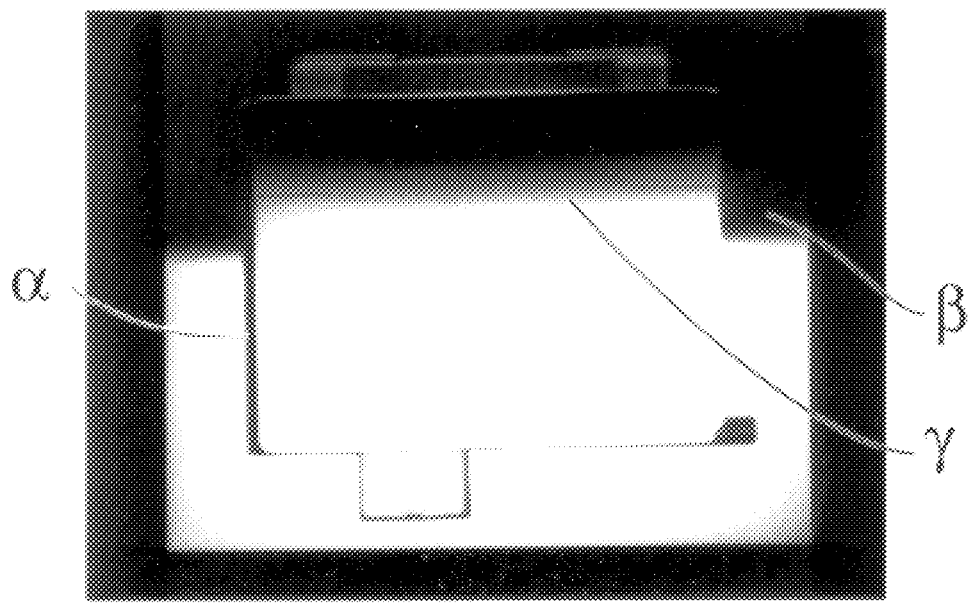
FIGS. 4A and 4B schematically show an image of an optical element to be inspected, visually indicated on a display, in the case where an illumination unit of the optical element inspecting apparatus is too close to the optical element.
Figure 4B:
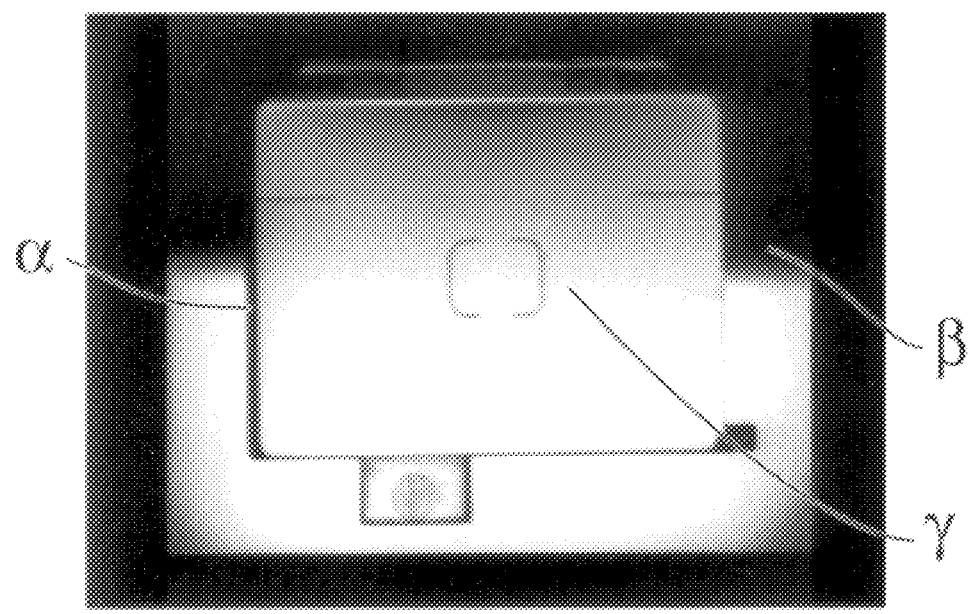
Figure 4C:
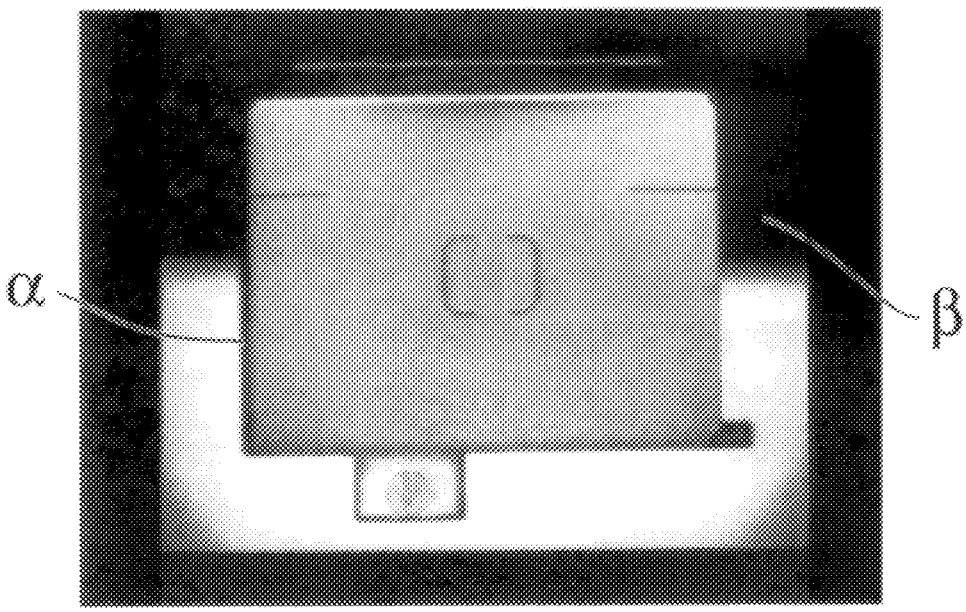
FIG. 4C schematically shows another image of the optical element to be inspected, visually indicated on the display, in the case where the illumination unit has been adjusted to be at an appropriate position.
Figure 4D:
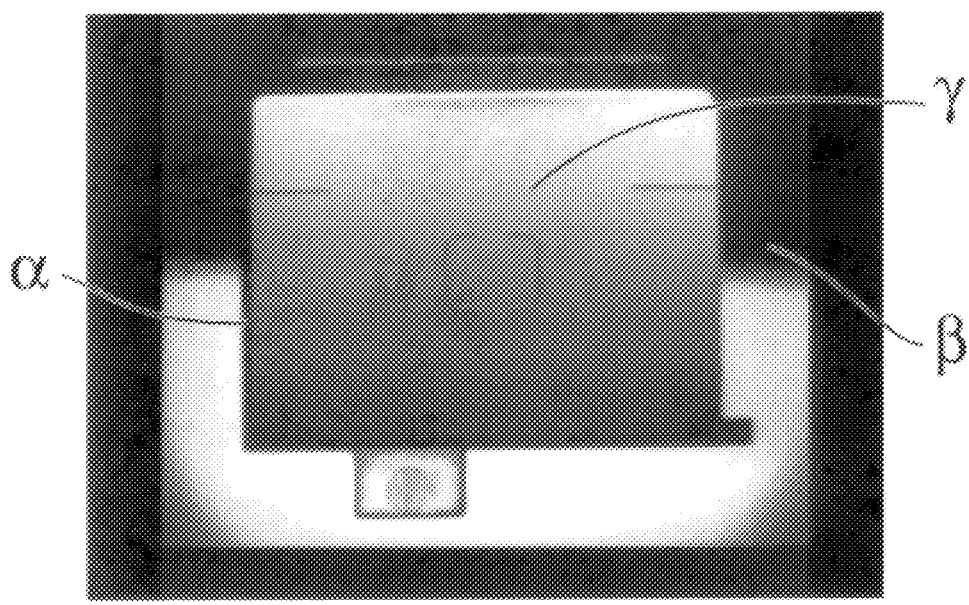
FIGS. 4D and 4E schematically show another image of the optical element to be inspected, visually indicated on the display, in the case where the illumination unit is too far away from the optical element.
Figure 4E:
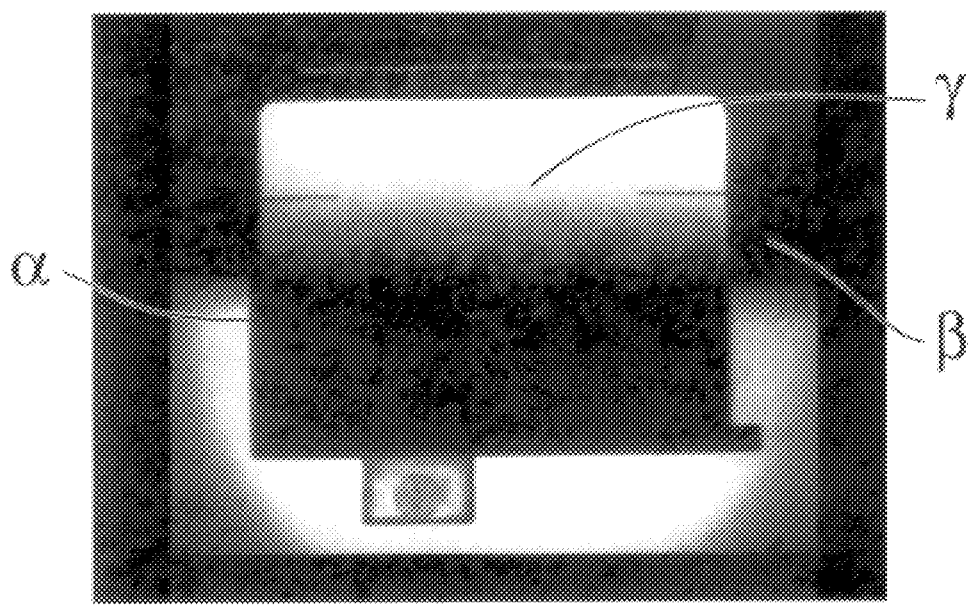
Figure 5:
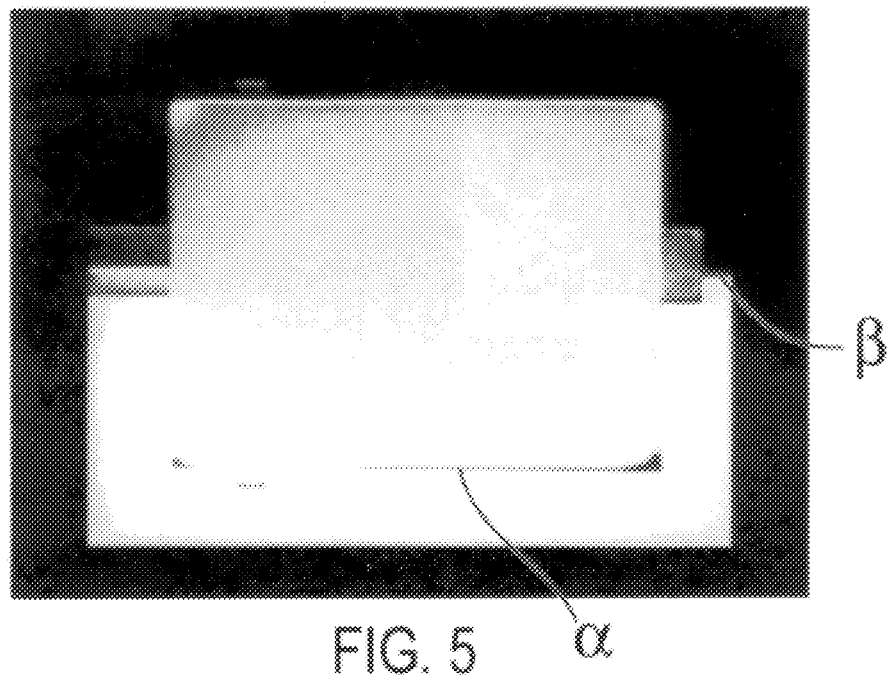
FIG. 5 schematically shows an image of the optical element to be inspected, visually indicated on the display, in the case of the optical element having no optical defect.

Inside the real image a of the optical element "A" (or the optical element "B"), if the focal point of the optical element "A" (or the resultant focal point of the lens group consisting of the optical element "B" and the correction lens "C") is shifted toward the image pickup apparatus 7 from the position of the light interceptive pattern 6a, a slightly blurred real image (erect image) γ of the light interceptive pattern 6a is formed inside the real image α (see FIGS. 4D and 4E). The degree of blurring of the real image (erect image) γ of the light interceptive pattern 6a increases and decreases as the deviation of the focal point decreases (FIG. 4D) and increases (FIG. 4E), respectively.

Conversely, if the focal point of the optical element "A" (or the resultant focal point of the lens group consisting of the optical element "B" and the correction lens "C") is shifted toward the optical fiber bundle 3 from the position of the light interceptive pattern 6a, a slightly blurred real image (inverted image) γ of the light interceptive pattern 6a is formed inside the real image α (see FIGS. 4A and 4B). The degree of blurring of the real image (inverted image) γ of the light interceptive pattern 6a increases and decreases as the deviation of the focal point decreases (FIG. 4B) and increases (FIG. 4A), respectively.

When the focal point of the optical element "A" (or the resultant focal point of the lens group consisting of the optical element "B" and the correction lens "C") is identical to the position of the light interceptive pattern 6a, the portion inside the real image α becomes the most blurred, so that the light is emitted entirely at uniform brightness (FIG. 4C).

On the display 10, the portion inside the real image α of the outer peripheral edge of the optical element is indicated as a grey plane having a uniform density, since the black portion of the light interceptive pattern 6a (produced by the interception of the white light) and the white portion (produced by the transmission of the white light) are uniformly mixed, provided that the optical element "A" or "B" has no optical defect (in case of a spherical lens; see FIG. 4C). Note that if the optical element "A" or "B" to be inspected is an aspherical lens, an image whose brightness gradually and slightly varies is obtained since the focal point gradually varies. As the focal point shifts from the light interceptive pattern 6a along the optical axis O, the black and white portions of the light interceptive pattern 6a are apart from each other, resulting in the formation of a clear image of the light interceptive pattern 6a.

Inspection Process of an Optical Element by the Optical Element Inspecting Apparatus of the First Embodiment Upon inspecting the optical element using the inspecting apparatus of the first embodiment, an inspector attaches the optical element "A" or "B" to a holder (not shown) and positions the same coaxially on the optical axis O. In the case of the optical element being an optical element other than the convex lens "A", the correction lens "C" is inserted between the optical element "B" and the illumination unit 4.

The inspector turns on the white light lamp 1 to illuminate the light interceptive pattern 6a of the light intercepting plate 6. Consequently, the image picked up by the image pickup element 9 is indicated on the display 10.

Thereafter, the inspector moves the illumination unit 4 while observing the image on the display 10. Each of FIGS. 4A through 4E shows an image indicated on the display 10 in the case of a rectangular-shaped biconvex lens made of a synthetic resin whose front and rear surfaces are each spherical surfaces. If the real image γ of the light interceptive pattern 6a appears in the real image α of the optical element on the same side (on the upper side in FIG. 4A or 4B) as the real image β of the light interceptive pattern which appears outside the real image α of the optical element, as shown in FIG. 4A or 4B, the illumination unit 4 is too close to the optical element, and hence the illumination unit 4 is adjusted to be moved away from the optical element. Conversely, if the real image γ of the light interceptive pattern 6a appears in the real image α of the optical element on the opposite side of the real image β of the light interceptive pattern which appears outside the real image α of the optical element, as shown in FIG. 4D or 4E, the illumination unit 4 is too far away from the optical element, and hence the illumination unit 4 is adjusted to be moved closer to the optical element. As a result of the adjustment of the position of the illumination unit 4, if a substantial part of the real image γ of the light interceptive pattern 6a disappears in the real image α of the optical element as shown in FIG. 4C, it can be considered that the illumination unit 4 is appropriately positioned, and hence the adjustment of the illumination unit 4 ends.

In the optical element inspecting apparatus of the first embodiment, the illumination unit 4 can be adjusted to move along the optical axis O. Therefore, according to the optical element inspecting apparatus of the first embodiment, different types of optical elements having different focal lengths can be inspected. Furthermore, not only a convex lens but also a concave lens can be inspected by using the correction lens "C". Additionally, even if the focal length of a convex lens is long, the convex lens can be inspected by making the distance between the convex lens and the illumination unit 4 short by moving the illumination unit 4.

As a result of the adjustment of the position of the illumination unit 4 as noted above, the position where the illumination unit 4 is positioned is substantially equivalent to the focal point of the optical element "A" (or the resultant focal point of the lens group consisting of the optical element "B" and the correction lens "C"). Therefore, in the case where the optical element "A" or "B" has no optical defect, the density of color becomes even, entirely in the real image α of the optical element.

Figure 6:
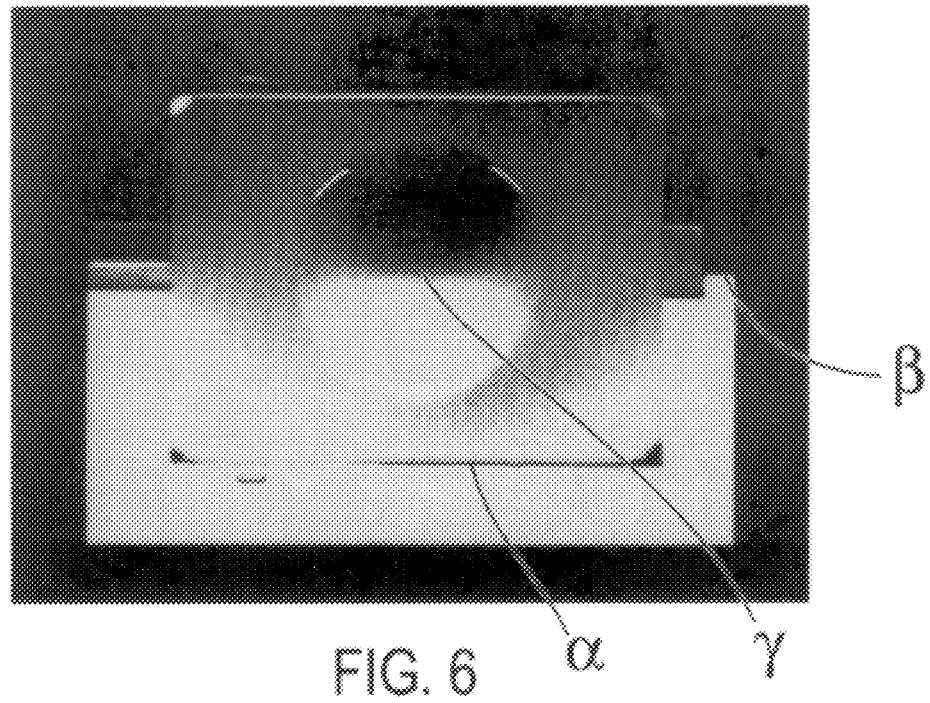
FIG. 6 schematically shows an image of the optical element to be inspected, visually indicated on the display, in the case of the optical element having a depression.

However, if the optical element "A" or "B" has a portion whose refractive index or refracting power is abnormal due to a surface defect or an imperfect shape, it is deemed that the defective portion has a focal length different from that of the normal portion. Therefore, the real image γ of the light interceptive pattern 6a only appears on the defective portion, as shown in FIG. 6. The irregularity (abnormality) of the refractive index (refracting power) can be recognized depending upon the appearance of the real image γ of the light interceptive pattern 6a. Namely, as the irregularity of the refractive index (refracting power), i.e., the deviation of the focal length, becomes larger, the density pattern of the image of the light interceptive pattern 6a becomes more clear.

For instance, a depression sometimes occurs on an optical element usually in the form of a circular shape, and the focal length becomes longer at the portion of the optical element where the depression appears since the thickness of the optical element at that portion is thinner than the other portions having no depression. Therefore, the real image γ of the light interceptive pattern 6a seen in the image of the depression in the form of a circular shape can be seen on the display 10, as shown in FIG. 6, and the real image γ corresponding to the abnormal portion (portion having the depression) of the optical element, can be seen on the same side as the real image β of the light interceptive pattern 6a which appears outside the real image α. Therefore, in the case when such an image as shown in FIG. 6 is seen, it can be judged that there is a depression.

The effect of jetting may cause irregularities in the shape of the optical element, and may cause the refractive index to vary irregularly. Thus, the portion of an optical element having an irregular shape seen on the display 10 causes a great variation in brightness. Therefore, that portion causing a great variation in brightness can be judged to be the portion where jetting has occurred.

As can be understood from the foregoing, according to the optical element inspecting apparatus of the first embodiment, a slight difference in refractive index of the optical element "A" or "B" to be inspected is converted into a difference in color density seen on the display 10, on which the variation of the refractive index is perceived. Furthermore, since the shape of a defect of the optical element is recognized by seeing the shape of the portion, corresponding to the defect, which is seen on the display 10, not only the defect but also the type and degree thereof can be recognized.

If the surface of the optical element "A" or "B" to be inspected is scratched or has a foreign matter attached thereto, an image of the defect (scratch, foreign matter, etc.) is formed inside the real image α of the optical element by the image pickup lens 8. Namely, if the light is intercepted by the foreign matter (dust, etc.), a shadow darker than the remaining portion is formed, and if the light is diverged by the scratch, bright areas are formed.

The inventors of the present invention have found through experimentation that in the case where the edges of the light interceptive pattern (i.e., boundary lines between the black-painted portions and the transparent portions) extend only in one direction it is difficult for the optical element inspecting apparatus to detect the optically abnormal factor which extends in a direction normal to that direction in which the edges of the light interceptive pattern extend. However, according to the optical element inspecting apparatus of the first embodiment, since the light interceptive pattern 6a is printed on the light intercepting plate 6 such that the edges of the light interceptive pattern 6a extend perpendicular to one another, optically abnormal factors extending in various directions can be detected.

Figure 7:
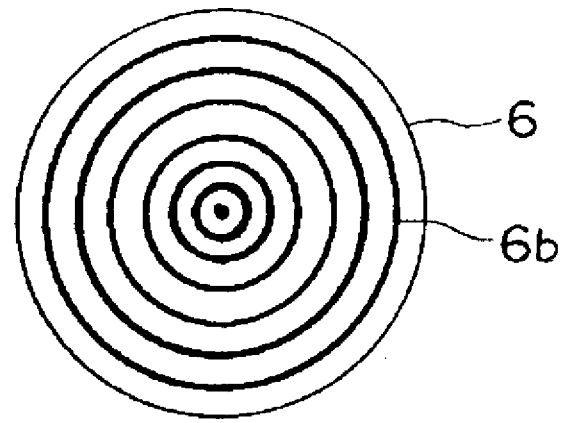
FIG. 7 is a front elevational view of another light intercepting pattern.

FIG. 7 shows another embodiment of the light interceptive pattern, namely, a light interceptive pattern 6b whose printed pattern is different from that of the light interceptive pattern 6a. The light interceptive pattern 6b may be printed on the light intercepting plate 6 instead of the aforementioned light interceptive pattern 6a. The light interceptive pattern 6b is formed such that a plurality of concentric circles are printed on the light intercepting plate 6 with the optical axis O being a center of the circles. Therefore, the edges of the light interceptive pattern 6b extend in not only one or two directions but in various directions throughout 360 degrees. Therefore, according to the light interceptive pattern 6b, optically abnormal factors extending in various directions can be detected substantially with an equal detecting ability for each abnormal factor. Hence, the optically abnormal factors can be more precisely detected.

Figure 8:
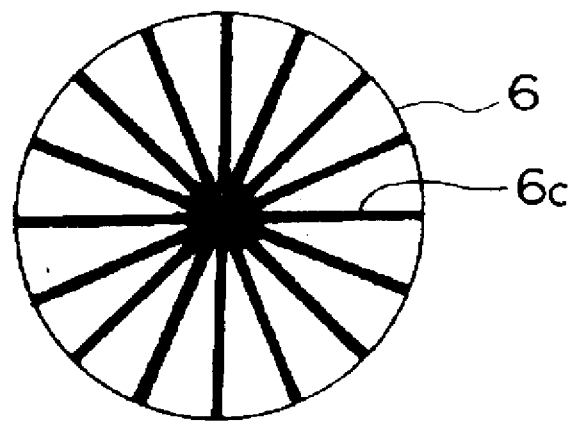
FIG. 8 is a front elevational view of yet another light intercepting pattern.

FIG. 8 shows yet another embodiment of the light interceptive pattern, namely, a light interceptive pattern 6c whose printed pattern is different from those of the light interceptive patterns 6a and 6b. The light interceptive pattern 6c may be printed on the light intercepting plate 6 instead of the aforementioned light interceptive pattern 6a. The light interceptive pattern 6c is formed such that a plurality of lines extending radially at regular intervals are printed on the light intercepting plate 6 with the optical axis O being a center of the lines. Therefore, according to the light interceptive pattern 6c, similar to the light interceptive pattern 6b, optically abnormal factors extending in various directions can be detected substantially with an equal detecting ability for each abnormal factor, and the optically abnormal factors can be precisely detected.

As can be understood from the foregoing, according to the optical element inspecting apparatus of the first embodiment, not only the abnormality in a refractive index of an optical element, but also a defect on the surface of the optical element, can be detected in a single inspection operation. Moreover, since the defect is emphasized to be clearly indicated on the display so as to discriminate the defective optical element from non-defective optical elements, a precise judgement can be carried out by an operator. Furthermore, since the position and shape of the defect is indicated as the image seen on the display, the type of the defect and also the degree of the defect can be recognized, which makes it possible to realize an appropriate feedback to the manufacturing process of the optical elements.

Figure 9:
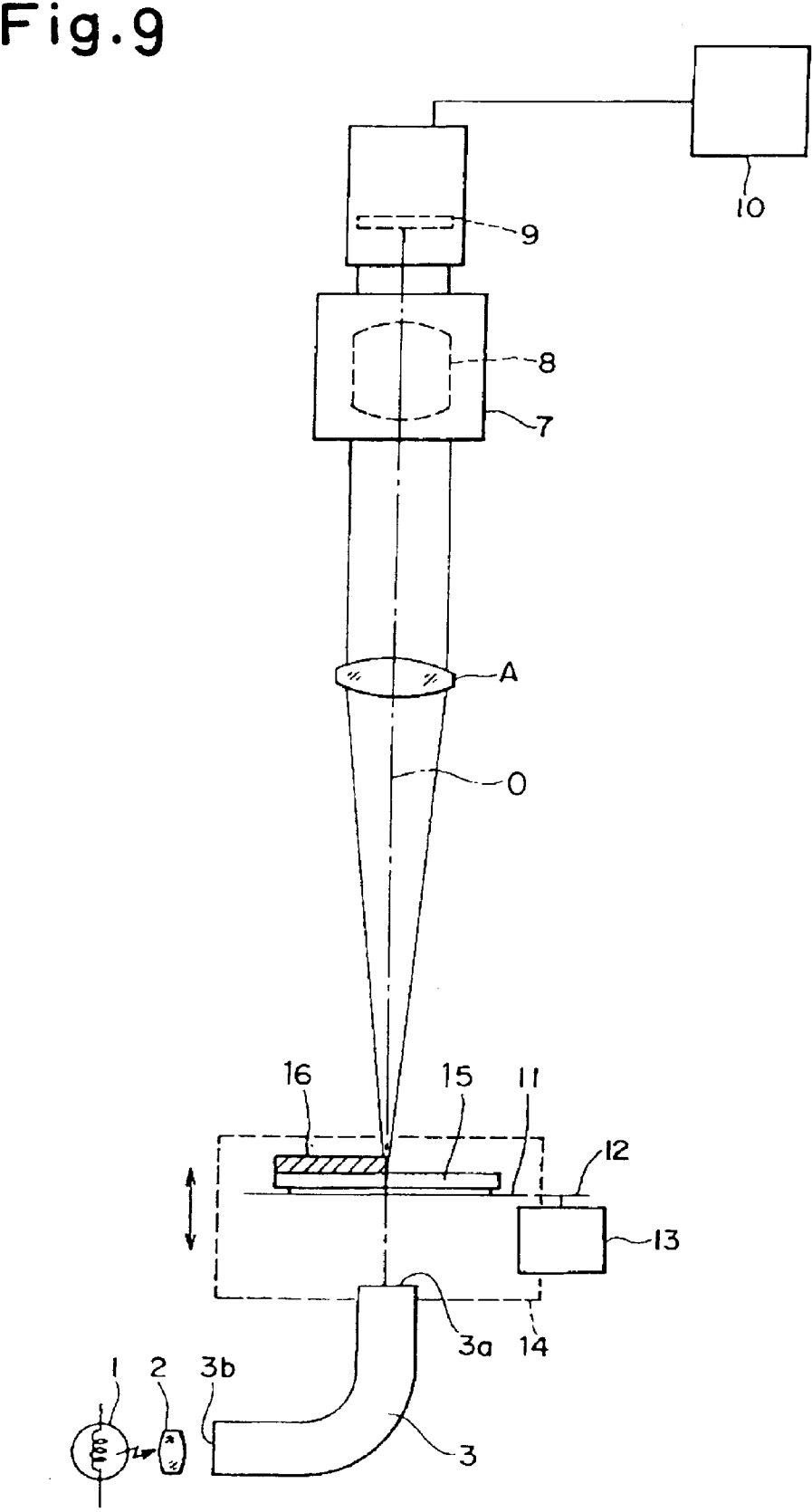
FIG. 9 is a schematic view of a second embodiment of an optical element inspecting apparatus to which the present invention is applied.
Figure 10:
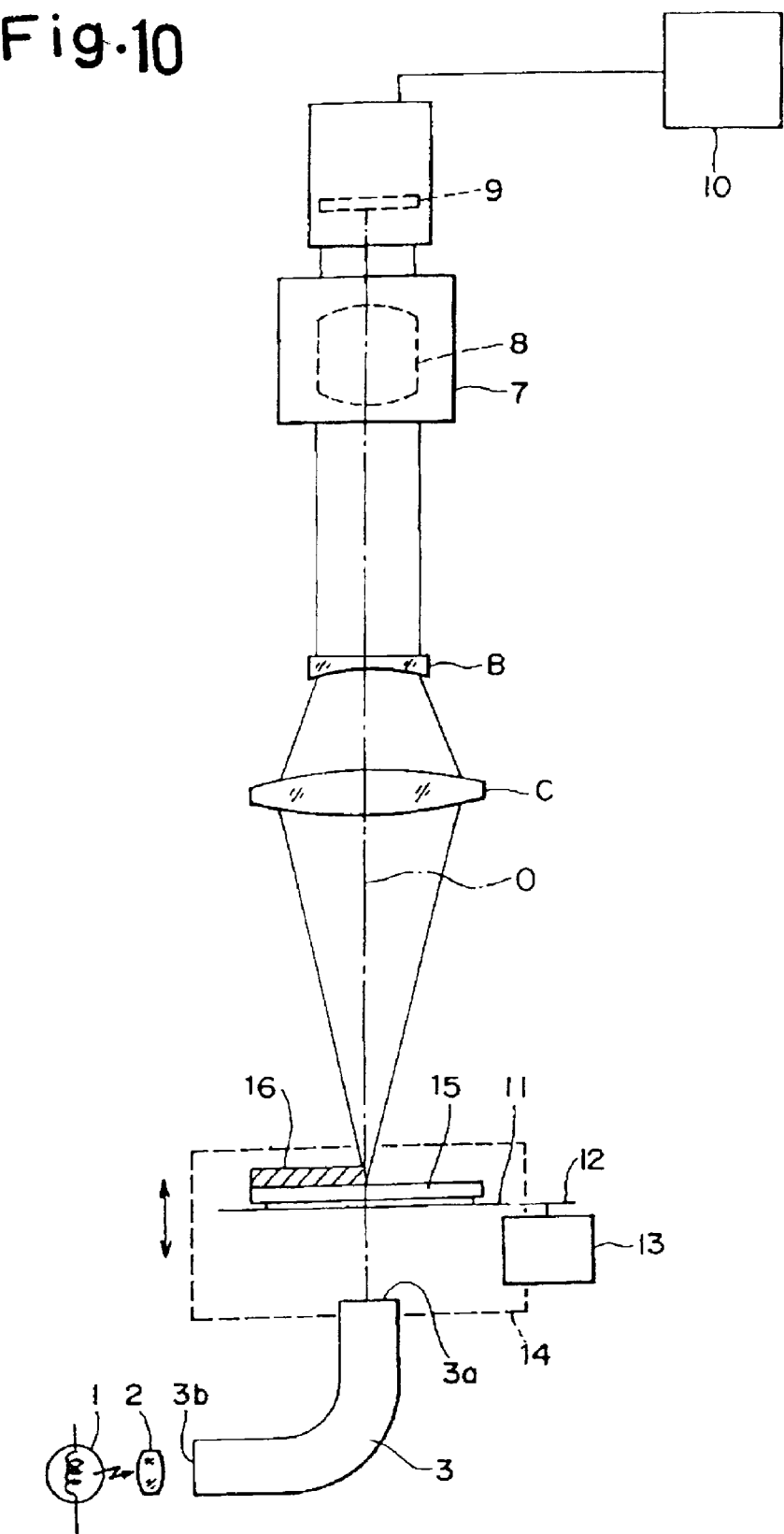
FIG. 10 is a schematic view of the optical element inspecting apparatus shown in FIG. 9, applied to a concave lens.
Figure 11:
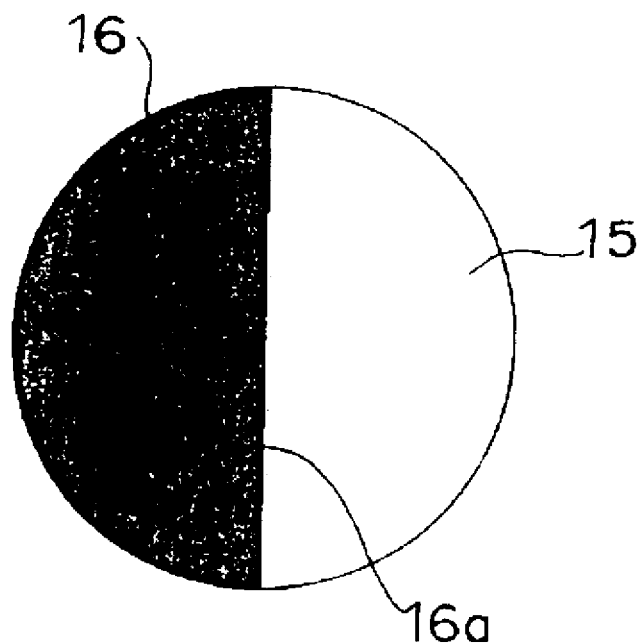
FIG. 11 is a front elevational view of a diffusion disc, on which a light intercepting plate is attached, shown in FIG. 9 or 10.

Optical Arrangement of Optical Element Inspecting Apparatus of Second Embodiment FIGS. 9 and 10 show a second embodiment of an optical element inspecting apparatus to which the present invention is applied. Since the optical element inspecting apparatus of the second embodiment is similar to the optical element inspecting apparatus of the first embodiment, only those structures different from the first embodiment will be hereinafter discussed.

Figure 12:
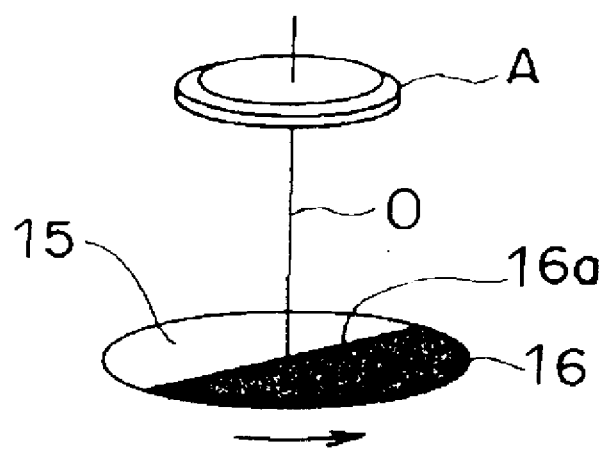
FIG. 12 is a perspective view of the diffusion disc shown in FIG. 11 and an inspection lens shown in FIG. 9 or 10.

An illumination unit 14, which corresponds to the illumination unit 4 of the first embodiment, is used in the second embodiment. Similar to the illumination unit 4, the illumination unit 14 is guided, by guiding means (not shown), along the optical axis O. The illumination unit 14 is provided therein with a circular diffusion disc 15, which corresponds to the diffusion disc 5 of the first embodiment. The diffusion disc 15 is rotatably supported in the illumination unit 14 about the optical axis O in a plane extending perpendicular to the optical axis O. The diffusion disc 15 is provided, on the surface facing in the direction of the image pickup apparatus 7, with a light intercepting plate 16 integrally cemented thereto. The light intercepting plate 16 serves as a light intercepting means. The light intercepting plate 16 is made of a semi-circular opaque plate, and is fixed on the diffusion disc 15 such that a radially-extending straight edge of the light intercepting plate 16 formed as a knife-edge (chord) 16a crosses the optical axis O, as shown in FIG. 12. The length of the knife-edge 16a is identical to the diameter of the diffusion disc 15, and the arc of the light intercepting plate 16 is accordingly concentrical to the peripheral edge of the diffusion disc 15. With such a structure, the light diffused by the diffusion disc 15 is partly intercepted by the light intercepting plate 16, while the remaining portion of the diffused light passes through without being interrupted by the light intercepting plate 16.

The illumination unit 14 is further provided therein with an annular gear 11. The annular gear 11 is coaxially fixed on the diffusion disc 15. The annular gear 11 meshes with a drive pinion 12 fixed on a rotating shaft of a motor 13. The motor 13 is fixed on the illumination unit 14. When the motor 13 is driven to rotate the rotating shaft thereof, the diffusion disc 15 rotates about the optical axis O, through the annular gear 11 and the pinion 12, in a plane normal to the optical axis O. The plane normal to the optical axis O includes a boundary plane between the diffusion disc 15 and the light intercepting plate 16. Consequently, the knife-edge 16a rotates about the optical axis O, as shown in FIG. 12. The revolving speed of the diffusion disc 15 has been adjusted to be 1 Hz (i.e., one rotation per second), for example. The motor 13, the annular gear 11 and the drive pinion 12 constitute a rotating means.

The length of the optical fiber bundle 3 is sufficiently longer than the displacement of the illumination unit 14. Thus, the optical fiber bundle 3 is extended in accordance with the movement of the illumination unit 14 so as to continuously illuminate the knife-edge 16a.

When the optical element to be inspected is positioned coaxial to the optical axis O between the image pickup apparatus 7 and the illumination unit 14, if the optical element to be inspected is a convex lens "A", the optical element is positioned such that the focal point thereof is coincident with the position of the knife-edge 16a, as shown in FIG. 9. If the optical element to be inspected is a concave lens "B", a correcting lens "C" made of a convex lens having a power (absolute value) greater than the power (absolute value) of the concave lens "B" is positioned between the concave lens "B" and the illumination unit 14, as shown in FIG. 10, in a similar manner to the first embodiment. The concave lens "B" and the correction lens "C" define a converging lens system whose resultant focal point is coincident with the position of the knife-edge 16a of the light intercepting plate 16. Namely, the focal point of the optical system including the optical element to be inspected is identical to the position of the light intercepting means, similar to the first embodiment.

If the optical element to be inspected (i.e., the convex lens "A" or the concave lens "B" and the correction lens "C") is positioned as mentioned above, the light emitted from the optical element (i.e., the convex lens "A" or the concave lens "B") becomes parallel beams of light so long as the optical element is a non-defective product. Consequently, if the knife-edge 16a of the light intercepting plate 6 is viewed from the side of the image pickup apparatus 7, the knife-edge 16a appears to be at infinity.

If the focal point of the optical element "A" (or the resultant focal point of the lens group consisting of the optical element "B" and the correction lens "C") is shifted toward the image pickup apparatus 7 from the position of the knife-edge 16a, an inverted image (real image) of the knife-edge 16a is formed in an area defined between the optical element "A" (or "B") and the image pickup lens 8 of the image pickup apparatus 7. The inverted image of the knife-edge 16a is relayed through the image pickup lens 8 to form an erect image (real image) of the knife-edge 16a in the area defined on the side of the image pickup lens 8 adjacent to the image pickup element 9. Conversely, if the focal point of the optical element "A" (or the resultant focal point of the lens group consisting of the optical element "B" and the correction lens "C") is shifted toward the optical fiber bundle 3 from the position of the knife-edge 16a, an erect image (virtual image) of the knife-edge 16a is formed in an area defined on the side of the light intercepting plate 16 adjacent to the optical fiber bundle 3. The erect image (virtual image) of the knife-edge 16a is relayed through the image pickup lens 8 to form an inverted image (real image) of the knife-edge 16a in the area defined on the side of the image pickup lens 8 adjacent to the image pickup element 9. Namely, the focal point of the optical element "A" to be examined (or the resultant focal point of the lens group consisting of the optical element "B" to be examined and the correction lens "C") defines a boundary position in which the object image (image of the knife-edge 16a) is formed as an erect image or an inverted image in the area defined on the side of the image pickup lens 8 adjacent to the image pickup element 9. Namely, in this position, the image is optically unstable.

The distance between the optical element to be inspected and the image pickup lens 8 is set to be as long as possible, so that the inverted image (real image) of the knife-edge 16a can be formed between the optical element and the image pickup lens 8 (precisely speaking, between the focal points thereof), if the focal point of the optical element "A" (or the resultant focal point of the lens group consisting of the optical element "B" and the correction lens "C") is slightly shifted toward the image pickup apparatus 7 from the position of the knife-edge 16a.

Thus, a real image (inverted image) α of the peripheral edge of the optical element to be examined is always formed on the image pickup element 9 and a slightly blurred real image (inverted image) β of the knife-edge 16a, which is directly visible without passing through the optical element, is formed around the real image α, as can be seen in FIGS. 4A through 4E, similar to the first embodiment.

Inside the real image α of the optical element "A" (or the optical element "B"), if the focal point of the optical element "A" (or the resultant focal point of the lens group consisting of the optical element "B" and the correction lens "C") is shifted toward the image pickup apparatus 7 from the position of the knife-edge 16a, a slightly blurred real image (erect image) γ of the knife-edge 16a is formed inside the real image α (see FIGS. 4D and 4E). The degree of blur of the real image (erect image) γ of the knife-edge 16a increases and decreases as the deviation of the focal point decreases (FIG. 4D) and increases (FIG. 4E) respectively.

Conversely, if the focal point of the optical element "A" (or the resultant focal point of the lens group consisting of the optical element "B" and the correction lens "C") is shifted toward the optical fiber bundle 3 from the position of the knife-edge 16a, a slightly blurred real image (inverted image) γ of the knife-edge 16a is formed inside the real image α (see FIGS. 4B and 4A). The degree of blur of the real image (inverted image) γ of the knife-edge 16a increases and decreases as the deviation of the focal point decreases (FIG. 4B) and increases (FIG. 4A), respectively.

When the focal point of the optical element "A" (or the resultant focal point of the lens group consisting of the optical element "B" and the correction lens "C") is identical to the position of the knife-edge 16a, the portion inside the real image α becomes the most blurred, so that the light is emitted entirely at uniform brightness (FIG. 4C).

On the display 10, the portion inside the real image α of the outer peripheral edge of the optical element is indicated as a grey plane having a uniform density since the black portion of the light intercepting plate 16 (produced by the interception of the white light) and the white portion (produced by the transmission of the white light) are uniformly mixed, provided that the optical element "A" or "B" has no optical defect (in case of a spherical lens; see FIG. 4C). Note that if the optical element "A" or "B" to be inspected is an aspherical lens, an image whose brightness gradually and slightly varies is obtained since the focal point gradually varies. As the focal point shifts from the knife-edge 16a along the optical axis O, the black portion due to the knife-edge 16a and the white portion due to the uncovered portion of the diffusion disc 15 are apart from each other, resulting in the formation of a clear image of the knife-edge 16a.

Inspection Process of Optical Element by Optical Element Inspecting Apparatus of Second Embodiment Upon inspecting the optical element using the inspecting apparatus of the second embodiment, an inspector attaches the optical element "A" or "B" to a holder (not shown) and positions the same coaxially on the optical axis O. In the case of the optical element being an optical element other than the convex lens "A", the correction lens "C" is inserted between the optical element "B" and the illumination unit 14.

The inspector turns on the white light lamp 1 to illuminate the knife-edge 16a of the light intercepting late 16. Consequently, the image picked up by the image pickup element 9 is indicated on the display 10.

Thereafter, the inspector moves the illumination unit 14 while observing the image on the display 10. Each of FIGS. 4A through 4E shows an image indicated on the display 10 in the case where a rectangular-shaped biconvex lens made of a synthetic resin whose front and rear surfaces are each spherical surfaces, as noted above. If the real image γ of the knife-edge 16a appears in the real image α of the optical element on the same side (on the upper side in FIG. 4A or 4B) as the real image β of the knife-edge 16a which appears outside the real image α of the optical element, as shown in FIG. 4A or 4B, the illumination unit 14 is too close to the optical element, and hence the illumination unit 14 is adjusted to be moved away from the optical element. Conversely, if the real image γ of the knife-edge 16a appears in the real image α of the optical element on the opposite side of the real image β of the knife-edge 16a which appears outside the real image α of the optical element, as shown in FIG. 4D or 4E, the illumination unit 14 is too far from the optical element, and hence the illumination unit 14 is adjusted to be moved closer to the optical element. As a result of the adjustment of the position of the illumination unit 14, if a substantial part of the real image γ of the knife-edge 16a disappears in the real image α of the optical element as shown in FIG. 4C, it can be considered that the illumination unit 14 is appropriately positioned, and hence the adjustment ends. Accordingly, in the optical element inspecting apparatus of the second embodiment, the illumination unit 14 can be adjusted to move along the optical axis O. Therefore, according to the optical element inspecting apparatus of the second embodiment, different types of optical elements having different focal lengths can be inspected.

As a result of the adjustment of the position of the illumination unit 14 as noted above, the position where the illumination unit 14 is placed is substantially equivalent to the focal point of the optical element "A" (or the resultant focal point of the lens group consisting of the optical element "B" and the correction lens "C"). Therefore, in the case where the optical element "A" or "B" has no optical defect, the density of color becomes even, entirely in the real image α of the optical element.

However, if the optical element "A" or "B" has a portion whose refractive index or refracting power is abnormal due to the surface defect or an imperfect shape, it is deemed that the defective portion has a focal length different from that of the normal portion. Therefore, the real image γ of the knife-edge 16a appears only on the defective portion, as shown in FIG. 6. The irregularity (abnormality) of the refractive index (refracting power) can be recognized depending upon the appearance of the real image γ of the knife-edge 16a. Namely, as the irregularity of the refractive index (refracting power), i.e., the deviation of the focal length, becomes large, the density pattern of the image of the knife-edge 16a becomes more clear.

For instance, a depression sometimes occur on an optical element usually in the form of a circular shape, and the focal length becomes longer at the portion of the optical element where the depression appears since the thickness of the optical element at that portion is thinner than the other portions having no depression, as noted above. Therefore, the real image γ of the knife-edge 16a seen in the image of the depression in the form of a circular shape can be seen on the display 10, as shown in FIG. 6, and the real image γ corresponding to the abnormal portion (portion having the depression) of the optical element, can be seen on the same side as the real image β of the knife-edge 16a which appears outside the real image α. Therefore, in the case when such an image as shown in FIG. 6 is seen, it can be judged that there is a depression.

The effects of jetting may cause irregularities in the shape of the optical element, and may cause the refractive index to vary irregularly, as noted above. Thus, the portion of an optical element having an irregular shape seen on the display causes a great variation in brightness. Therefore, that portion causing a great variation in brightness can be judged to be the portion where jetting has occurred.

As can be seen from the foregoing, according to the optical element inspecting apparatus of the second embodiment, similar to the first embodiment, a slight difference in refractive index of the optical element "A" or "B" to be inspected is converted into a difference in color density seen on the display 10, on which the variation of the refractive index is perceived. Furthermore, since the shape of a defect of the optical element is recognized by seeing the shape of the portion, corresponding to the defect, which is seen on the display, not only the defect but also the type and degree thereof can be recognized.

After the operator has adjusted the illumination unit 14 to be at an appropriate position, the operator operates a drive circuit (not shown) to actuate the motor 13 so as to rotate the rotating shaft thereof. By the actuation of the motor 13 the diffusion disc 5 together with the light intercepting plate 6 starts to rotate about the optical axis O at a revolving speed of 1 Hz, so that the direction of extension of the knife-edge 16a continuously changes. Due to the rotation of the knife-edge 16a about the optical axis O, if optical defects (i.e., portions in the image of the optical element that are observed on the display 10, the portions having a large difference in color density as compared with the peripheral portions) in different directions exist on the optical element, those optical defects are successively indicated on the display 10 in accordance with the extending direction of the knife-edge 16a. In the case where the knife-edge 16a is positioned on the optical axis O, the abnormal factor of the optical element in a direction parallel to the knife-edge 16a is greatly emphasized to be seen on the display 10, whereas the abnormal factor of the optical element in a direction perpendicular to the knife-edge 16a is hardly emphasized to be seen on the display 10. However, in the optical element inspecting apparatus of the second embodiment, since the knife-edge 16a rotates about the optical axis O in a plane extending normal to the optical axis O, abnormal factors of the optical element which extend in various directions can be emphasized to be indicated on the display 10 at a substantially common emphasizing level for each abnormal factor. Specifically, in the case where the optical element to be inspected is an aspherical lens, the portion of the lens where the optical element inspecting apparatus can clearly indicate abnormal factors is limited to a small area on the lens if the knife-edge 16a is stationary. However, since the knife-edge 16a rotates about the optical axis O in a plane extending normal to the optical axis O, abnormal factors of the optical element on the entire surface of the lens can be equally emphasized to be indicated on the display 10.

In the optical element inspecting apparatus of the second embodiment, since the knife-edge 16a is rotated at a predetermined revolving speed (1 Hz), the relative difference in degree of the abnormal factors in different directions on the optical element can be recognized by observing the images of the abnormal factors indicated on the display 10. Furthermore, even if a defect existing on the optical element is minute causing only a slight change in the refractive index of the optical element, that minute defect can be easily found by the operator since the color density of the image of the defect continuously changes on the display 10 in accordance with the rotation of the knife-edge 16a.

As can be seen from the foregoing, according to the optical element inspecting apparatus of the second embodiment, not only the abnormality in refractive index of an optical element but also the defect on the surface of the optical element can be detected in a single inspection operation. Moreover, since the defect is emphasized to be clearly indicated on the display so as to discriminate the defective optical element from non-defective optical elements, a precise judgement can be carried out by an operator. Furthermore, since the position and shape of the defect is reflected on the image of the defect seen on the display, the type of the defect and also the degree of the defect can be recognized, which makes it possible to realize an appropriate feedback to the manufacturing process of the optical elements. Still furthermore, an optical defect in any direction can be detected due to the rotational movement of the light intercepting plate.

Optical Arrangement of Optical Element Inspecting Apparatus of Third Embodiment

Figure 13:
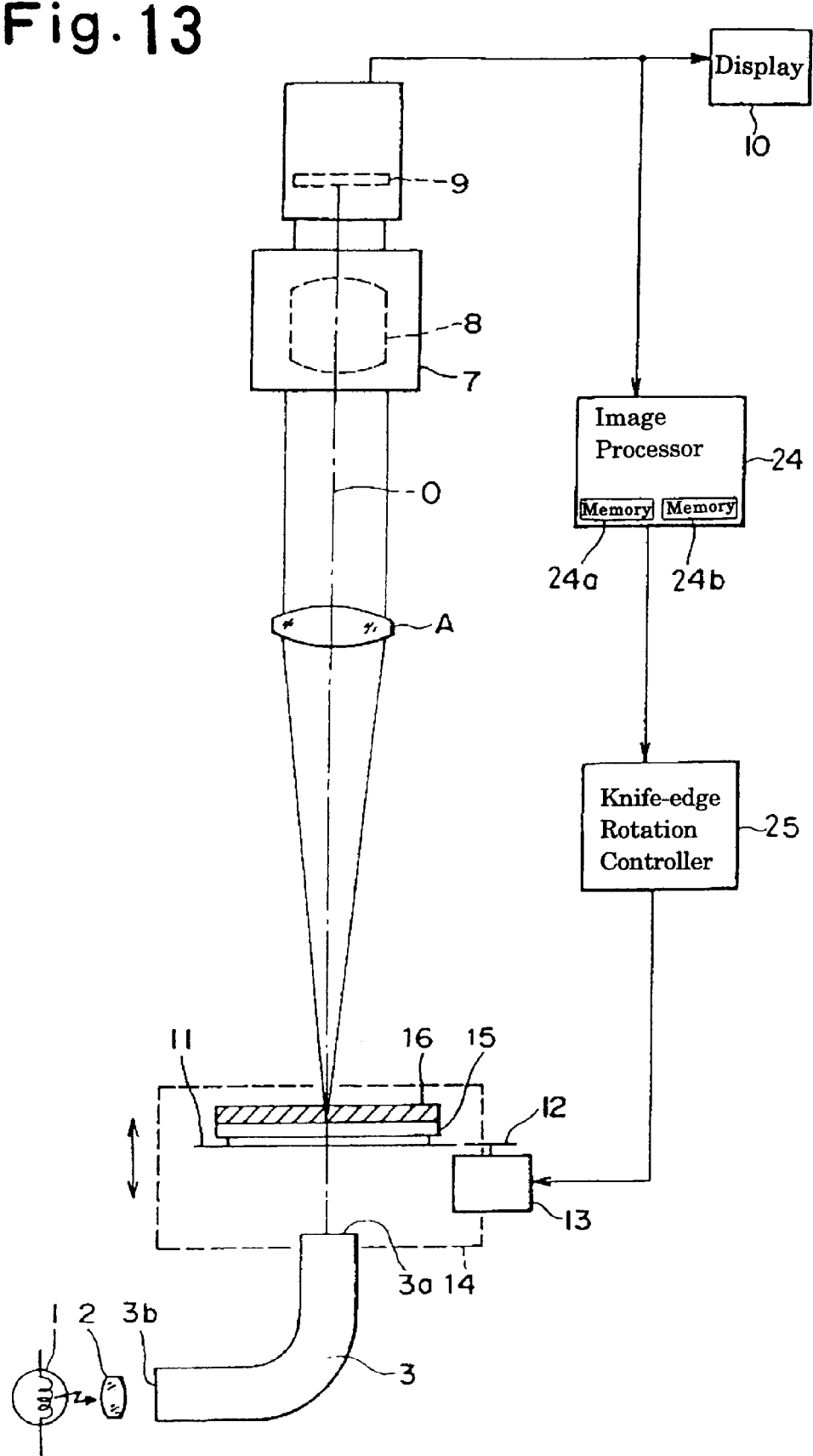
FIG. 13 is a schematic view of a third embodiment of an optical element inspecting apparatus to which the present invention is applied.
Figure 14:
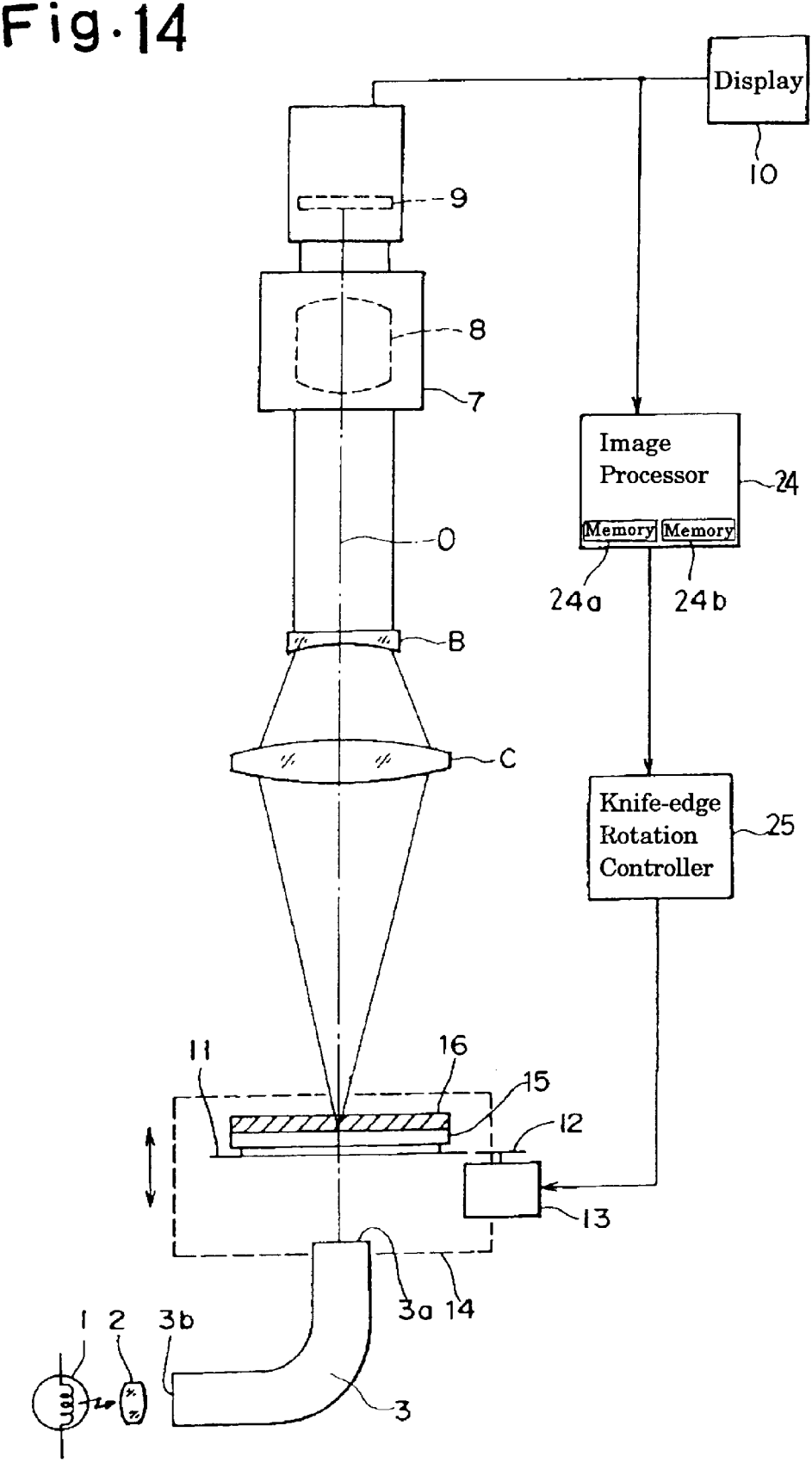
FIG. 14 is a schematic view of the optical element inspecting apparatus shown in FIG. 13, applied to a concave lens.

FIGS. 13 and 14 show a third embodiment of an optical element inspecting apparatus to which the present invention is applied. Since the optical element inspecting apparatus of the third embodiment is similar to the optical element inspecting apparatus of the second embodiment, only those structures different from the second embodiment will be hereinafter discussed.

In the third embodiment, the optical element inspecting apparatus is further provided with an image processor 24 and a knife-edge rotation controller 25 as shown in FIG. 13 or 14. The image picked up by the image pickup element 9 is input to both the display 10 and the image processor 24.

In the third embodiment, the display 10 is used only when an initial adjustment of the optical element inspecting apparatus (i.e., adjustment of the position of the illumination unit 14) is carried out.

The image processor 24 judges whether an optical element to be inspected is defective. Namely, the image data input from the image pickup device 9 is processed by the image processor 24 in which the degree of the optical defect of the optical element is converted into a numerical value or data which is compared with a predetermined reference value for judgement (allowable limit), to check whether the numerical data is above or below the reference value. The image processor 24 functions as an emphasizing means (emphasizer), a combining means (combiner), a digitizing means (digitizer), and a judging means. The image processor 24 also sends an instruction signal to the knife-edge rotation controller 25 to rotate the motor 13.

The knife-edge rotation controller 25 controls the motor 13 to rotate the rotating shaft thereof incrementally at an angular pitch of 22.5°, in accordance with the commands from the image processor 24.

Figure 15:
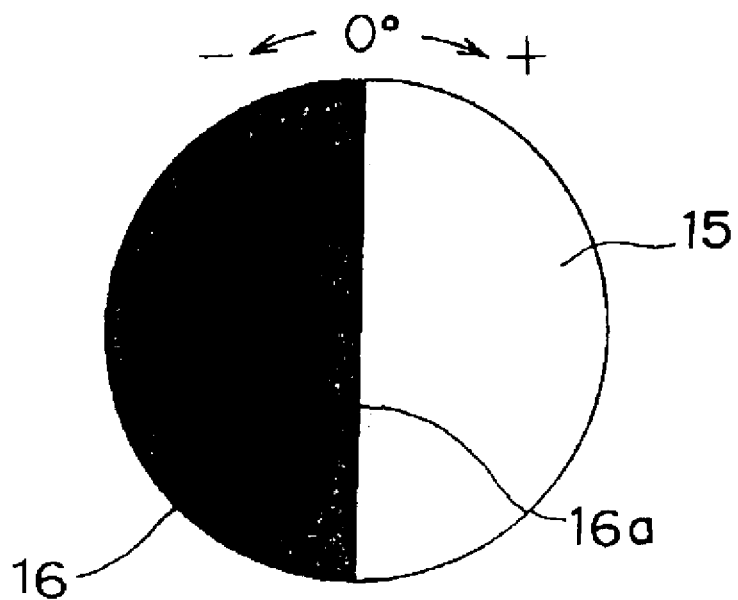
FIG. 15 is a front elevational view of a diffusion disc, on which a light intercepting plate is attached, shown in FIG. 13 or 14.
Figure 16:
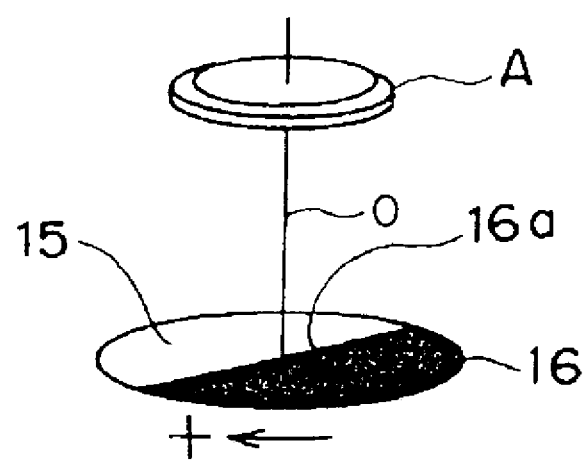
FIG. 16 is a perspective view of the diffusion disc shown in FIG. 15 and an inspection lens shown in FIG. 13 or 14.

When the motor 13 is driven by the knife-edge rotation controller 25, the diffusion disc 15 rotates in a plane perpendicular to the optical axis O (i.e., a plane in which a contact surface between the diffusion disc 15 and the light intercepting plate 16 lies), through the gear engagement between the gears 11 and 12, as shown in FIGS. 15 and 16. Note that the rotational direction of the diffusion disc 15 in this case is in the clockwise direction as viewed from the side of the image pickup apparatus 7. Consequently, the knife-edge 16a of the light intercepting plate 16 is rotated about the optical axis 1. The image processor 24, the knife-edge rotation controller 25, the motor 13, and the gears 11 and 12 constitute a rotating means.

Image Processing Operation

Figure 17:
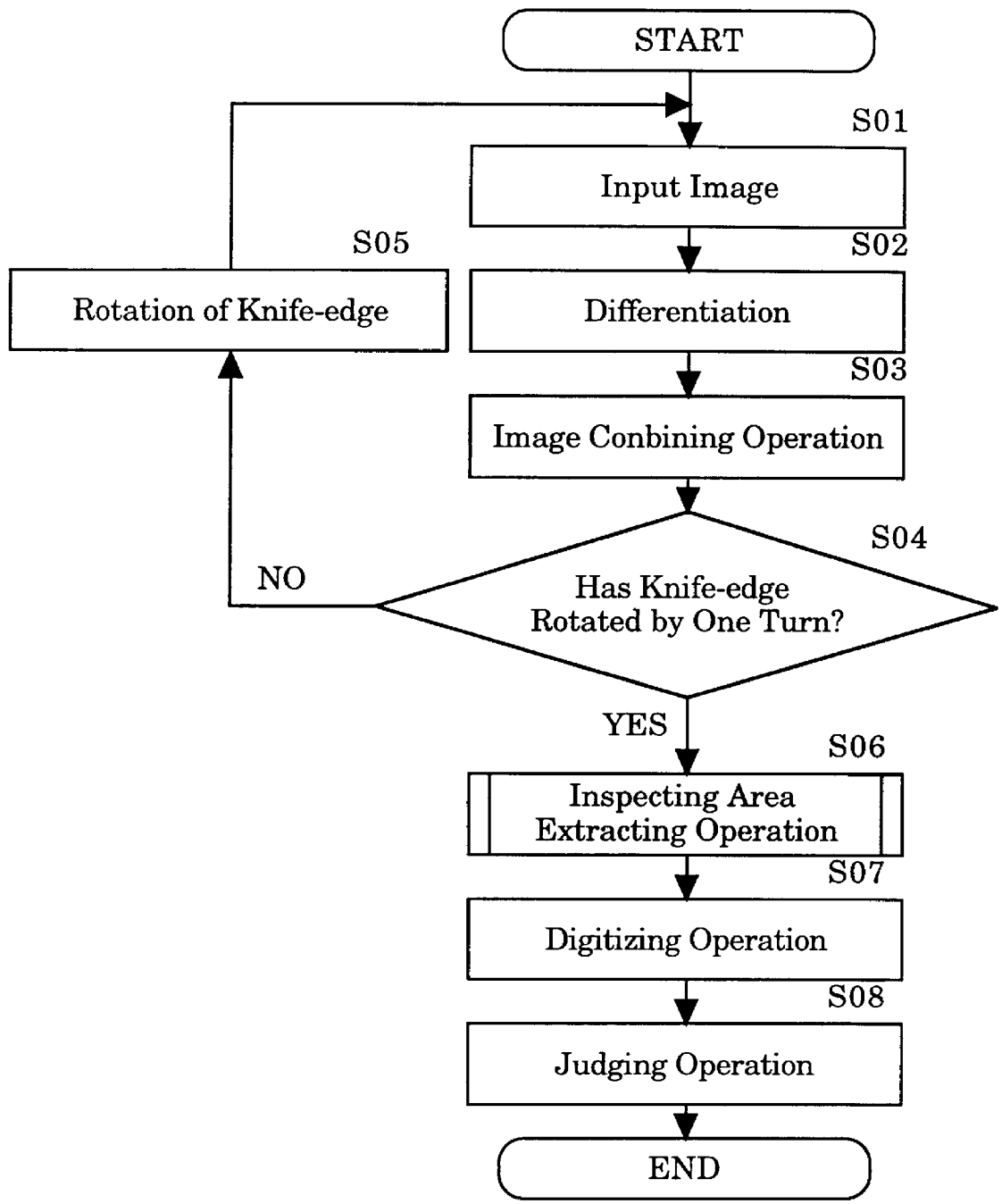
FIG. 17 is a flow chart of an image processing operation carried out by an image processor shown in FIG. 13 or 14.

The following discussion will be addressed to an image processing operation in the image processor 24 to judge whether the optical element is defective or non-defective, with reference to a flow chart shown in FIG. 17.

The image processing operation begins when an inspection start button (not shown) connected to the image processor 24 is depressed. Namely, the loop of operations from step S01 to step S05 is performed.

At step S01, the brightness of each pixel constituting the image data, supplied from the image pickup device 9, is converted into numerical data having 256 graduations and is stored in a first memory 24a provided in the image processor 24.

At step S02, the numerical data stored in the memory 24a is successively scanned and differentiated. Namely, the numerical values of the pixels are successively checked starting from the uppermost left pixel and moving toward the lowermost right pixel of the image. The numerical value of the pixel being checked is compared with the numerical values of the left and upper pixels adjacent thereto. The absolute values of the differences between the numerical values are selected to be differential values of the pixels to be checked (0–255). In the image data represented by the differential values thus obtained, only the images of the contour of the defective portion of the optical element and the edge of the knife-edge 16a have a high density (this corresponds to the aforementioned emphasizing means for emphasizing the portion of the image whose density considerably varies as a portion which represents the optical defect).

At step S03, an image combining operation is carried out. Namely, the differential values obtained at step S02 are written in a second memory 24b provided in the image processor 24. In the case that the differential values of the previous image have been written in the second memory 24b as a result of the previous operation at step S03, the stored differential values are fetched and added to the differential values obtained at step S02. Thereafter, the resultant values are again written in the memory 24b (this corresponds to the aforementioned image combining means for combining the images which have been picked up by the image pickup means and emphasized by the aforementioned emphasizing means during one rotation of the light intercepting means).

At step S04, whether or not the knife-edge 16a has rotated by one turn is checked. If a complete rotation of the knife-edge has not occurred, the control proceeds to step S05 to command the knife-edge rotation controller 25 to rotate the knife-edge 16a by 22.5°. If the image data obtained after the rotation of the knife-edge 16a is input from the image pickup device 9, the control is returned to step S01 to perform a new data processing operation.

The reason why the image data obtained by each slight angular displacement of the knife-edge 16a is accumulated (step S03) as mentioned above, will now be described. Namely, when the linear knife-edge 16a is inserted in the optical path, the abnormal component in the direction parallel to the length of the knife-edge 16a can be effectively detected, but the abnormal component in a direction perpendicular to the length of the knife-edge 16a can not be sufficiently detected. This is the reason why the abnormal components in all directions are detected while rotating the knife-edge 16a in a plane perpendicular to the optical axis O and are combined in the same image. Consequently, the following effect can be obtained. Namely, in an image obtained when the knife-edge 16a is stopped, the density of the image suddenly changes at the edge of the knife-edge 16a (laterally extending monochromatic boundary line in FIG. 6) and the edge of the defective portion (central circular portion in FIG. 6). The edge of the knife-edge 16a is not a subject to be inspected and hence should not be detected. To this end, the knife-edge 16a is rotated. Namely, when the knife-edge 16a is rotated, the edge of the knife-edge 16a is rotated, but no defective portion is moved. Accordingly, if the image combining operation is carried out, the edge of the defective portion is locally emphasized, while the edge of the knife-edge 16a is averaged in a plane within a closed area (surrounded by the edge) of the defective portion, so that the edge of the knife-edge 16a cannot be recognized as a boundary line.

Upon completion of one rotation of the knife-edge, i.e., upon completion of 16 intermittent angular displacements of the knife-edge 16a at a pitch of 22.50°, the control proceeds to step S06 from step S04.

Figure 18:
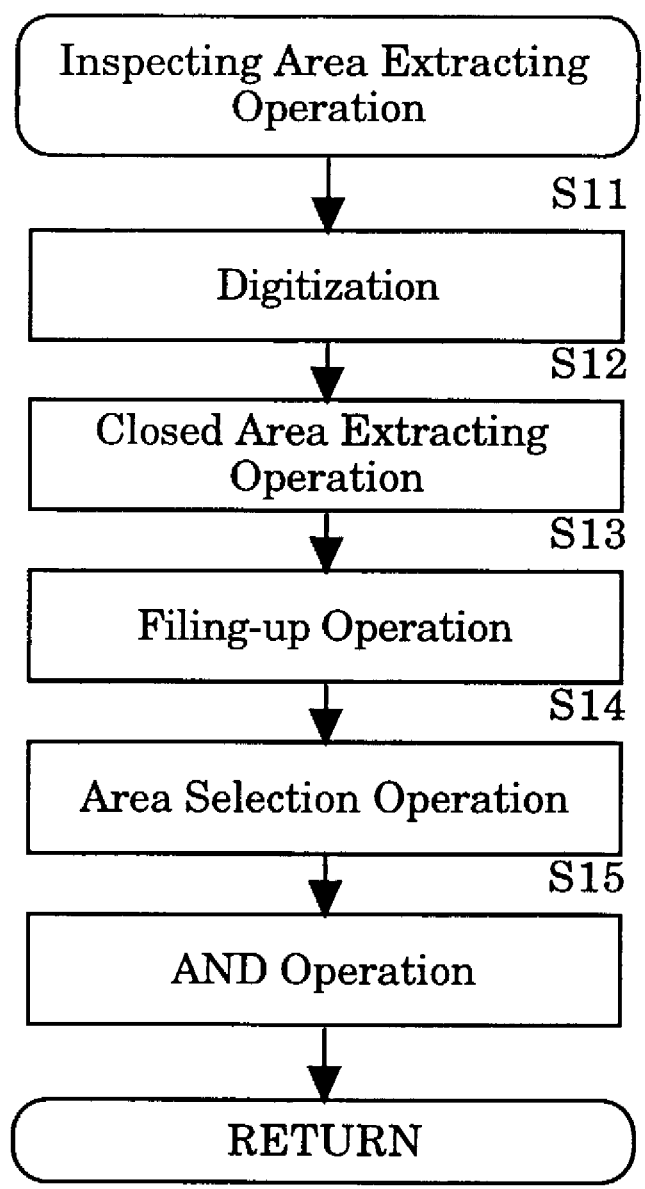
FIG. 18 is a flow chart of a subroutine for an inspection area extracting operation carried out at step S06 in FIG. 17.
Figure 19A:
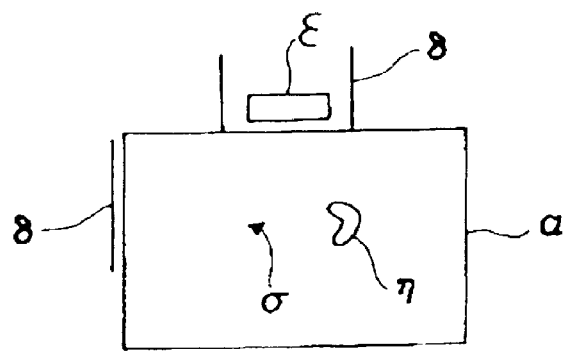
FIGS. 19A–19D are explanatory views of an inspection area extracting operation shown in FIG. 18.

FIG. 18 shows a sub-routine of an inspection area extracting operation which is carried out at step S06. In this sub-routine, a digitizing operation is effected at step S11. In the digitizing operation, the numerical data corresponding to each pixel of the image data in the second memory 24b is replaced by the value 255 (white) or 0 (black) depending upon whether the numerical value is above or below a predetermined threshold value, respectively. The threshold value is determined such that the real image α of the peripheral edge of the optical element to be inspected defines a closed continuous curve of white pixels (255). The image data obtained by digitization is shown in FIG. 19A. In FIG. 19A, "δ" represents the image of a gate upon plastic molding of the optical element, "ε" represents the image of a pattern on the gate, "ζ" represents the image of the defective portion (irregular refractive index) due to jetting, etc., and "σ" represents the image of dust affixed to the surface of the optical element. Note that in FIGS. 19A through 19D, the white/black pattern is inverted for the purpose of illustration.

Figure 19B:

At step S12, a closed area extracting operation is carried out. In this operation, only the area surrounded by the closed white line is extracted. Namely, among the black pixels (0) which constitute the binary image data digitized at step S11, those surrounded by the white pixels (255) are deemed to be pixels within the closed area. The numerical values of the pixels in the closed area are set to be 255 and the numerical values of the remaining pixels are set to be 0. The image data obtained by the closed area extracting operation is shown in FIG. 19B. As can be seen in FIG. 19B, the lines (image) δ having open ends are erased, but the closed lines (images) ζ and σ remain since the inversion of the white/black image only takes place in the image α of the closed edge of the optical element.

Figure 19C:

At step S13, a filling-up operation is carried out. In this operation, the black pixels (0) remaining in the white pixels (255) are erased. Namely, among the black pixels (0) which constitute the image data obtained at step S12, the numerical values of those surrounded by the white pixels (255) are set to be 255. The image data obtained by the filling-up operation is shown in FIG. 19C. As can be seen in FIG. 19C, the closed lines (images) ζ and σ in the image α are erased, and only the black images α and ε remain.

Figure 19D:
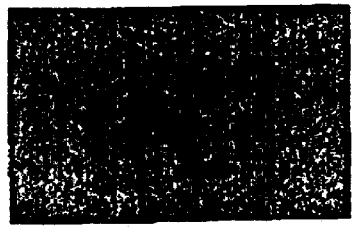

At step S14, an area selecting operation is effected. In this operation, only the necessary areas are made effective and the remaining closed areas are erased. Namely, among the closed areas contained in the image data obtained at step S13, the numerical values of the pixels constituting the closed areas located at the center portion of the image surface are maintained as they are, and the numerical values of the pixels constituting the remaining closed areas are set to be (0). The image data thus obtained is shown in FIG. 19D. As shown in FIG. 19D, the area of the white pixels (255) corresponds to the area of the image of the optical element to be inspected. This image will be referred to as a mask image.

At step S15, an AND operation of the numerical values (8-bit parallel digital values) of the pixels which constitute the mask image and the numerical values (8-bit parallel digital values) of the pixels stored in the second memory 24b, is performed. As a result of the AND operation, the portions of the image data corresponding to the white pixels (255) of the mask image are maintained as they are and the numerical values of the remaining pixels are all set to 0.

Thus, image data which is used to judge whether the optical element is defective or non-defective is obtained. The sub-routine ends and the control is returned to the main routine shown in FIG. 17.

In FIG. 17, at step S07, the numerical values of the pixels that constitute the image data extracted at step S06 are compared with the threshold value whose level is set so as not to extract mold-transferred noise, and are digitized (255: white, or 0: black). Namely, if the numerical value of each pixel which constitutes the image data is greater (i.e., lighter) than the threshold value, the numerical value is replaced with 255, and if the numerical value of each pixel is less (i.e., darker) than the threshold value, the numerical value is replaced with 0. Thereafter, figure characteristic amounts (surface area, maximum width, center of gravity, horizontal/vertical Feret's diameters, etc., of the white portion) of the digitized image data are calculated. For example, the number of white pixels (255) defines the surface area amount (this corresponds to the aforementioned digitizing means for digitizing the defective portion of the optical element in the image picked up by the image pickup means).

In the process of producing a plastic optical element such as a plastic lens, a lens molding method ("injecting molding") is carried out in which a mold made by a cutting process, using a cutting tool, is used to mold the plastic optical element. Due to the cutting process, even if the mold is carefully and accurately produced, minute cut marks or grooves are inevitably formed on the cut surface of the mold. As a result, marks corresponding to the cut marks are formed on the surface of the plastic optical element when it is molded. The aforementioned "mold-transferred noise" refers to the image data of such marks formed on the surface of the plastic optical element as a result of the cutting process. Such marks formed on the plastic optical element are minute and thus do not deteriorate the desired optical property of the plastic optical element. However, since the sensitivity of detection of the optical element inspection apparatus of the present embodiment is high enough to pick up the image of the marks formed due to the cut marks, the sensitivity of detection (i.e., the aforementioned threshold value) accordingly needs to be set so as not to extract the aforementioned mold-transferred noise.

At step S08, a judging operation is carried out. Namely, the figure characteristics obtained at step S07 are compared with predetermined judgement criteria (reference values). If the amount of at least one figure characteristic is above the corresponding reference value, it is judged that the optical element is defective. If all the figure characteristic amounts are below the respective reference values, it is judged that the optical element is non-defective (this corresponds to the aforementioned judging means for judging whether the numerical value obtained by the digitizing means is above the reference value). Note that the figure characteristic amount to be used for the judgement is selected in accordance with the kind of optical element to be judged. When the judgement is complete, the image processing operation ends.

It is possible to conduct a MAX operation in place of the AND operation in the image combining operation at step S03. In the AND operation mentioned above, the numerical values of the corresponding pixels of the two image data to be combined are added, whereas in the MAX operation, the larger numerical value is selected from among the numerical values (brightness) of the corresponding pixels of the image data to be combined, and is used for the judgement. In the MAX operation, if the brightness of the image data to be combined is high, no saturation of the brightness of the combined image data takes place, thus resulting in a correct inspection.

Inspection Process of Optical Element by Optical Element Inspecting Apparatus of Third Embodiment Upon inspecting the optical element using the inspecting apparatus of the third embodiment, an inspector attaches the optical element "A" or "B" to a holder (not shown) and positions the same in the optical axis O. In the case of the optical element being an optical element other than the convex lens "A", the correction lens "C" is inserted between the optical element "B" and the illumination unit 14. The insertion of the correction lens "C", which is made of a convex lens, makes it possible to inspect the optical element "B" in the form of a concave lens. Note that if the convex lens "A" as an optical element to be inspected has a long focal length, the distance between the convex lens "A" and the illumination unit 14 can be shortened.

The inspector turns on the white light lamp 1 to illuminate the knife-edge 16a of the light intercepting plate 16. Consequently, the image picked up by the image pickup element 9 is indicated on the display 10.

Thereafter, the inspector moves the illumination unit 14 while observing the image on the display 10. If the real image γ of the knife-edge 16a appears in the real image α of the contour of the optical element on the same side (on the upper side in FIG. 4A or 4B) as the real image β of the knife-edge 16a which appears outside the real image α, as shown in FIG. 4A or 4B, the illumination unit 14 is too close to the optical element, and hence the illumination unit 14 is adjusted to move away from the optical element. Conversely, if the real image γ of the knife-edge 16a appears in the real image α of the contour of the optical element on the opposite side of the real image β of the knife-edge 16a which appears outside the real image α, as shown in FIG. 4D or 4E, the illumination unit 14 is too far from the optical element, and hence the illumination unit 14 is moved closer to the optical element. As a result of the adjustment of the position of the illumination unit 14, if a substantial part of the real image γ of the knife-edge 16a disappears in the real image α of the contour of the optical element as shown in FIG. 4C, it can be considered that the illumination unit 14 is appropriately positioned, and hence the adjustment ends. As can be understood from the foregoing, since the illumination unit 14 is movable in the optical axis direction in the illustrated embodiment, different kinds of optical elements having different focal lengths can be inspected.

Thereafter, the inspector depresses an inspection start button (not shown) to commence the image processing operation shown in FIG. 17. Consequently, the knife-edge 16a is intermittently rotated every 22.5° by the knife-edge rotation controller 25 (S05), and the image formed by the light transmitted through the optical element "A" or "B" is picked up by the image pickup apparatus 7 at each angular position (S01). The image processor 24 differentiates the portions of the image in which the density changes to emphasize the same (S02), and adds the data for one turn of the knife-edge 16a (S03, S04). Consequently, any areas of the image having defective components (irregular refractive index or refracting power, scratches, etc.) are extracted in any directions and are combined in one piece of image data. Namely, any portions having an optical defect are indicated as a white image on the display. The image data includes unnecessary data of portions other than the portions which function as an optical element. Nevertheless, the unnecessary data is erased by the inspection area extracting operation at step S06. The surface area or the maximum width, etc., of the defective portion are digitized and compared with a reference value. Consequently, whether the optical element is defective or non-defective can be objectively judged in accordance with the comparison result.

As may be understood from the above discussion, according to the optical element inspecting apparatus of the third embodiment, the judgement of the optical element can be carried out with reference to an objective criterion. Accordingly, the quality of non-defective products can be stabilized and there is no wastage of non-defective products.

Although the diffusion disc 5 or 15 is illuminated from one side (lower side as viewed from, e.g., FIG. 1) opposite to the other side (upper side as viewed from, e.g., FIG. 1) where the optical element to be inspected is positioned with respect to the diffusion disc 5 or 15 in each of the above embodiments, the diffusion disc 5 or 15 may be illuminated from above the other side, i.e., from the side where the optical element to be inspected is positioned.

In the second or third embodiment, although the aforementioned boundary line 16a is a straight boundary line, it may be a curved boundary line. The number of boundary lines is not limited to one but can be two or more which may be arranged in a stripe pattern. It is also possible to provide a plurality of boundary lines whose directions are different from each other (i.e., not parallel).

In the second or third embodiment, although the diffusion disc 15 is rotated together with the light intercepting plate 16 by the motor 13, a different structure may be adopted in which the diffusion disc 15 and the light intercepting plate 16 are separately provided and in which only the light intercepting plate 16 is rotated by the motor 13. The same performance can be expected with such a structure.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. An optical element inspecting apparatus for detecting an optical defect of an optical element to be inspected, comprising:

a diffusion plate;

means for emitting light towards said diffusion plate such that a diffused light diffused by said diffusion plate is incident upon an optical system including at least said optical element; and means for intercepting a part of said diffused light so that said part of said diffused light is not incident upon said optical system, said light intercepting means being positioned substantially in a plane perpendicular to an optical axis of said optical system, between said optical system and said diffusion plate, substantially at a focal point of said optical system.

2. The optical element inspecting apparatus according to claim 1, wherein said light intercepting means contacts a portion of said diffusion plate.

3. The optical element inspecting apparatus according to claim 2, wherein said light intercepting means is fixed to said diffusion plate.

4. The optical element inspecting apparatus according to claim 1, wherein said optical system consists of only said optical element.

5. The optical element inspecting apparatus according to claim 1, wherein said optical system comprises a converging lens system.

6. The optical element inspecting apparatus according to claim 1, wherein said optical system comprises a converging lens system, said converging lens system comprising said optical element and a correction lens said optical element being a concave lens, and said correction lens being a convex lens.

7. The optical element inspecting apparatus according to claim 1, wherein said light intercepting means comprises an opaque plate.

8. The optical element inspecting apparatus according to claim 7, wherein said opaque plate is shaped in the form of a semi-circle.

9. The optical element inspecting apparatus according to claim 1, wherein said light intercepting means comprises a transparent member and an opaque member, said opaque member being formed on said transparent member.

10. The optical element inspecting apparatus according to claim 9, wherein said opaque member comprises opaque paint on said transparent member.

11. The optical element inspecting apparatus according to claim 9, wherein said opaque member is formed as a grating.

12. The optical element inspecting apparatus according to claim 9, wherein said opaque member is formed as a plurality of concentric circles.

13. The optical element inspecting apparatus according to claim 9, wherein said opaque member is formed as a plurality of lines extending radially from a center of said diffusion plate.

14. The optical element inspecting apparatus according to claim 9, wherein said opaque member is formed as a semi-circle.

15. The optical element inspecting apparatus according to claim 1, further comprising image pickup means for picking up an image of light transmitted through said optical system, said image pickup means comprising an image pickup lens which converges said light transmitted through said optical system.

16. The optical element inspecting apparatus according to claim 15, wherein said image pickup means further comprises a CCD sensor, wherein said light transmitted through said optical system is converged by said image pickup lens on said CCD sensor.

17. The optical element inspecting apparatus according to claim 15, wherein said image pickup means is positioned at a first position which is optically equivalent to a second position where a surface of said optical element is located.

18. The optical element inspecting apparatus according to claim 1, wherein said diffusion plate is guided along said optical axis to adjust a position of said light intercepting means along said optical axis.

19. The optical element inspecting apparatus according to claim 1, further comprising means for rotating said light intercepting means in said plane perpendicular to said optical axis.

20. The optical element inspecting apparatus according to claim 19, wherein said rotating means rotates said light intercepting means intermittently.

21. The optical element inspecting apparatus according to claim 19, wherein said light intercepting means comprises a transparent portion through which a part of said light diffused by said diffusion plate can pass, and an opaque portion which intercepts a part of said light diffused by said diffusion plate, said transparent and opaque portions being separated by a straight boundary line.

22. The optical element inspecting apparatus according to claim 21, wherein said transparent and opaque portions are in the form of a circle and a semi-circle, respectively, said semi-circular opaque portion covering half of said circular transparent portion.

23. The optical element inspecting apparatus according to claim 21, wherein said rotating means rotates said light intercepting means about a rotational center lying on said straight boundary line.

24. The optical element inspecting apparatus according to claim 23, wherein said rotational center coincides with said optical axis.

25. The optical element inspecting apparatus according to claim 1, further comprising:

image pickup means for picking up an image of light transmitted through said optical system;

digitizing means for representing a portion of said image which corresponds to said optical defect of said optical element by a numerical value; and judging means for judging whether said numerical value is above a predetermined reference value.

26. The optical element inspecting apparatus according to claim 25, further comprising emphasizing means for emphasizing a portion of said image in which a color density varies considerably, as a portion that represents said optical defect.

27. The optical element inspecting apparatus according to claim 26, further comprising means for rotating said light intercepting means in said plane perpendicular to said optical axis.

28. The optical element inspecting apparatus according to claim 27, wherein said rotating means rotates said light intercepting means intermittently by a predetermined angle, and further wherein said image pickup means picks up said image at each angular position of said light intercepting means.

29. The optical element inspecting apparatus according to claim 28, further comprising image combining means for combining said images picked up by said image pickup means and emphasized by said emphasizing means during one rotation of said light intercepting means.

30. The optical element inspecting apparatus according to claim 26, wherein said emphasizing means separates said image into a plurality of pixels, and compares and differentiates brightness of adjacent pixels from said plurality of pixels, so that images obtained by said differentiating operation are deemed to be said emphasized images.

31. The optical element inspecting apparatus according to claim 25, wherein said digitizing means measures an area of said portion of said image to be said numerical value.

32. The optical element inspecting apparatus according to claim 25, wherein said digitizing means measures a maximum width of said portion of said image to be said numerical value.

33. The optical element inspecting apparatus according to claim 25, further comprising extracting means for extracting only a portion of said image that corresponds to said optical element from said image picked up by said image pickup means.

34. The optical element inspecting apparatus according to claim 15, further comprising a display on which said image picked up by said image pickup means is displayed.

35. An optical element inspecting apparatus for detecting an optical defect of an optical element to be inspected, comprising:

illuminating means;

a diffusion plate illuminated with light emitted from said illuminating means;

a plate having an opaque portion that is fixed on said diffusion plate;

image pickup means for picking up an image of said optical element; and a display on which said image picked up by said image pickup means is indicated, wherein said plate having said opaque portion is positioned substantially at a focal point of a converging optical system which includes at least said optical element.

36. An optical lens inspecting apparatus for detecting a defect of an optical element to be inspected, comprising:

a light source;

means for diffusing light emitted from said light source; and means for intercepting a portion of light emitted from said diffusing means, said intercepting means being positioned substantially at a focal point of a converging optical system which includes at least said optical element.

37. An optical element inspecting apparatus for detecting an optical defect of an optical element to be inspected, comprising:

surface illuminant for emitting light towards a converging optical system which includes at least said optical element; and means for intercepting a portion of said light so that said part of said light does not reach said converging optical system, said light intercepting means being positioned substantially in a plane perpendicular to an optical axis of said converging optical system between said converging optical system and said surface illuminant substantially at a focal point of said converging optical system.

38. The optical element inspecting apparatus according to claim 37, wherein said surface illuminant comprises a diffusion plate and means for emitting light towards said diffusion plate such that a diffused light diffused by said diffusion plate is incident upon said converging optical system.

* * * * *